US012537107B2

(12) United States Patent
Hettig et al.

(10) Patent No.: US 12,537,107 B2
(45) Date of Patent: Jan. 27, 2026

(54) MANAGING CAREGIVER MESSAGES

(71) Applicant: Hill-Rom Services, Inc., Batesville, IN (US)

(72) Inventors: Mark F. Hettig, Denver, CO (US); Justin Haldane, Tampa, FL (US)

(73) Assignee: Hill-Rom Services, Inc., Batesville, IN (US)

(*) Notice: Subject to any disclaimer, the term of this patent is extended or adjusted under 35 U.S.C. 154(b) by 361 days.

(21) Appl. No.: 17/453,273

(22) Filed: Nov. 2, 2021

(65) Prior Publication Data

US 2022/0139570 A1 May 5, 2022

Related U.S. Application Data

(60) Provisional application No. 63/109,464, filed on Nov. 4, 2020.

(51) Int. Cl.

*G16H 80/00* (2018.01)
*G16H 10/60* (2018.01)
*G16H 40/20* (2018.01)
*G16H 40/67* (2018.01)

(52) U.S. Cl.

CPC ............. *G16H 80/00* (2018.01); *G16H 10/60* (2018.01); *G16H 40/20* (2018.01); *G16H 40/67* (2018.01)

(58) Field of Classification Search

CPC ........ G16H 80/00; G16H 10/60; G16H 40/20; G16H 40/67; G06Q 10/10; G06Q 50/01; G06Q 50/22

USPC .......................................................... 705/2-3

See application file for complete search history.

(56) References Cited

U.S. PATENT DOCUMENTS

| | | | | |
|---|---|---|---|---|
| 5,961,446 | A | 10/1999 | Beller et al. | |
| 7,991,764 | B2 | 8/2011 | Rathod | |
| 8,095,381 | B2 | 1/2012 | Simons et al. | |
| 8,183,987 | B2 | 5/2012 | Traughber et al. | |
| 8,468,030 | B2 | 6/2013 | Stroup et al. | |
| 8,788,279 | B2 | 7/2014 | Hayes | |
| 8,965,327 | B2 | 2/2015 | Davis et al. | |
| 9,058,635 | B1 * | 6/2015 | Rybkin | G16H 10/60 |

(Continued)

FOREIGN PATENT DOCUMENTS

| | | | |
|---|---|---|---|
| CA | 2957237 | A1 | 8/2018 |
| CN | 102947857 | A | 2/2013 |

(Continued)

OTHER PUBLICATIONS

Aronsky, Supporting patient care in the emergency department with a computerized whiteboard system, 2007, J Am Med Inform Assoc. Mar.-Apr. 2008;15(2):184-94 (Year: 2007).*

(Continued)

*Primary Examiner* — Kambiz Abdi
*Assistant Examiner* — Tran N Nguyen
(74) *Attorney, Agent, or Firm* — Merchant & Gould P.C.

(57) ABSTRACT

A system for providing communications on mobile devices located in a healthcare facility receives a notification identifying a patient admitted to the healthcare facility, creates a patient-centric chat room based the notification, and adds caregivers to the patient-centric chat room. The system provides messaging communications in the patient-centric chat room, and terminates the patient-centric chat room after the patient is discharged from the healthcare facility.

10 Claims, 26 Drawing Sheets

(56) References Cited

U.S. PATENT DOCUMENTS

| | | | | |
|---|---|---|---|---|
| 9,147,041 | B2 | 9/2015 | Amarasingham et al. | |
| 9,647,968 | B2 | 5/2017 | Smullen et al. | |
| 9,782,075 | B2 | 10/2017 | Redei | |
| 10,231,622 | B2 | 3/2019 | Soyao et al. | |
| 10,257,277 | B2 | 4/2019 | Schlapfer et al. | |
| 10,325,679 | B2 | 6/2019 | MacDonald et al. | |
| 10,332,625 | B2 | 6/2019 | Ting et al. | |
| 10,496,788 | B2 | 12/2019 | Amarasingham et al. | |
| 10,496,790 | B2 | 12/2019 | Mark et al. | |
| 10,554,612 | B2 | 2/2020 | Yin | |
| 10,777,059 | B2 | 9/2020 | Herbst et al. | |
| 2005/0288965 | A1* | 12/2005 | Van Eaton | G16H 40/20 705/2 |
| 2011/0202974 | A1* | 8/2011 | Leader | G16H 10/60 726/28 |
| 2014/0039912 | A1* | 2/2014 | Turinas | H04W 12/06 705/2 |
| 2014/0058750 | A1* | 2/2014 | Fotsch | G16H 10/60 705/3 |
| 2014/0095210 | A1* | 4/2014 | Goss | G16H 10/60 705/3 |
| 2014/0164011 | A1 | 6/2014 | Guelich et al. | |
| 2015/0025904 | A1* | 1/2015 | Rao | G06Q 10/107 705/2 |
| 2015/0187037 | A1* | 7/2015 | Subramanian | G16H 10/60 705/2 |
| 2015/0310176 | A1 | 10/2015 | Chen et al. | |
| 2015/0363569 | A1 | 12/2015 | Ryan et al. | |
| 2016/0117464 | A1 | 4/2016 | Ito et al. | |
| 2016/0300033 | A1 | 10/2016 | Duke et al. | |
| 2017/0004273 | A1 | 1/2017 | Mbanefo et al. | |
| 2017/0116385 | A1 | 4/2017 | Lauderdale et al. | |
| 2017/0199973 | A1 | 7/2017 | Walton et al. | |
| 2017/0201475 | A1 | 7/2017 | Gupta et al. | |
| 2017/0300823 | A1 | 10/2017 | Bostick et al. | |
| 2018/0166172 | A1 | 6/2018 | Fidone et al. | |
| 2018/0197638 | A1* | 7/2018 | Blanshard | G16H 80/00 |
| 2018/0226157 | A1 | 8/2018 | Blanshard et al. | |
| 2018/0295186 | A1* | 10/2018 | Schlapfer | H04L 67/02 |
| 2018/0302231 | A1 | 10/2018 | Sung et al. | |
| 2019/0013097 | A1 | 1/2019 | Rho | |
| 2019/0108908 | A1 | 4/2019 | Faulks et al. | |
| 2019/0172566 | A1* | 6/2019 | Schulman | G16H 10/60 |
| 2019/0197861 | A1* | 6/2019 | Tunnell | A61B 5/0205 |
| 2019/0228867 | A1* | 7/2019 | Smyth | G16H 80/00 |
| 2019/0333613 | A1 | 10/2019 | Zaidi et al. | |
| 2019/0355447 | A1 | 11/2019 | Barkol et al. | |
| 2019/0362840 | A1 | 11/2019 | Eberting | |
| 2019/0392926 | A1 | 12/2019 | Koh et al. | |
| 2020/0106736 | A1 | 4/2020 | Nakamura et al. | |
| 2020/0176131 | A1 | 6/2020 | Shen | |
| 2020/0265070 | A1* | 8/2020 | Rapaport | G06Q 10/10 |
| 2021/0217106 | A1* | 7/2021 | Hauser | H04L 67/306 |
| 2021/0337166 | A1* | 10/2021 | John | H04L 51/52 |

FOREIGN PATENT DOCUMENTS

| | | | |
|---|---|---|---|
| CN | 103034780 | A | 4/2013 |
| CN | 107038326 | A | 8/2017 |
| WO | 2019070822 | A1 | 4/2019 |
| WO | 2019142975 | A1 | 7/2019 |

OTHER PUBLICATIONS

"Universally Connected Care Teams", DrFirst Unite the Healthiverse, accessed Sep. 25, 2020.

"Everybody benefits from cBoards", cBoards, Caresharing BV, www.cboardsapp.com, accessed Sep. 25, 2020.

"Empowering care teams with new tools in Microsoft 365", Williams, Emma, Microsoft365, Mar. 6, 2020.

Extended European Search Report for Application No. 21206560.1 mailed Apr. 8, 2022, 9 pages.

Chu et al., "Design and application of mobile medical information system based on information technology," Chinese Medical Equipment Journal, vol. 36, No. 5, pp. 53-56, 59 (2015) (in Chinese with English Translation).

Xu et al., "Brief Discussion on "Online Hospital" Management," Medical Information, vol. 18, No. 06, pp. 583-585 (2005) (in Chinese with English Translation).

* cited by examiner

MANAGING CAREGIVER MESSAGES

BACKGROUND

Caregivers, such as doctors, nurses, trained medical professions, and the like are typically assigned to multiple patients during a shift in a care facility such as a hospital. Various alerts or calls from patients and other caregivers are communicated to the caregivers who must prioritize and manage the incoming alerts. Other staff members such as those in housekeeping, food service, and patient transporting must also respond to various alerts and calls.

Sometimes caregivers and staff are provided with wireless communication devices, such as pagers or mobile phones, to receive incoming calls and alerts related to the care of one or more patients. At the end of their shift, the caregivers and staff must return these devices such as for recharging or for use by other caregivers and staff on subsequent shifts. More recently, it is common for caregivers and staff to bring their own mobile phones to work to communicate with each other during a shift for purposes of coordinating patient care.

SUMMARY

In general terms, the present disclosure relates to improving communications between caregivers in a healthcare facility. In one possible configuration, a system provides a technical effect by preventing the loss of information, comments, and details that are not typically entered into a patient's medical record, maintaining a history of caregiver communications across caregiver shifts, and allowing caregivers to tag other caregivers in messages sent to a chat room to ensure that the messages are seen while also reducing alert fatigue. Various aspects are described in this disclosure, which include, but are not limited to, the following aspects.

One aspect relates to a system for providing communications on mobile devices located in a healthcare facility. The system comprises: a computing device having at least one processor, and a memory storing instructions which, when executed by the at least one processor, cause the system to: receive a notification identifying a patient admitted to the healthcare facility; create a patient-centric chat room based on the notification; add caregivers to the patient-centric chat room, each of the caregivers added to the patient-centric chat room having a role that provides patient viewing privileges and being assigned to the patient or to the patient's location in the healthcare facility; provide messaging communications in the patient-centric chat room for the caregivers to communicate with each other; and terminate the patient-centric chat room after the patient is discharged from the healthcare facility.

Another aspect relates to a method for providing communications between caregivers located in a healthcare facility. The method comprises: receiving a notification identifying a patient admitted to the healthcare facility; creating a patient-centric chat room based on the notification; adding caregivers to the patient-centric chat room, each of the caregivers having a role providing patient viewing privileges, and being assigned to the patient or to the patient's location; and providing messaging communications in the patient-centric chat room for the caregivers to communicate with each other in the chat room.

Another aspect relates to a non-transitory computer readable storage media including computer readable instructions which, when executed by a computing device, cause the computing device to: create a chat room for a department, unit, or team within a healthcare facility; add caregivers to the chat room that are assigned to the department, unit, or team; provide messaging communications in the chat room for the caregivers to communicate with each other; monitor a status of the caregivers to remove caregivers from the chat room who have ended their shift, and add new caregivers to the chat room who have started their shift, and that are assigned to the department, unit, or team; and store the messaging communications from the chat room to a memory.

DESCRIPTION OF THE FIGURES

The following drawing figures, which form a part of this application, are illustrative of the described technology and are not meant to limit the scope of the disclosure in any manner.

DETAILED DESCRIPTION

Figure 1:
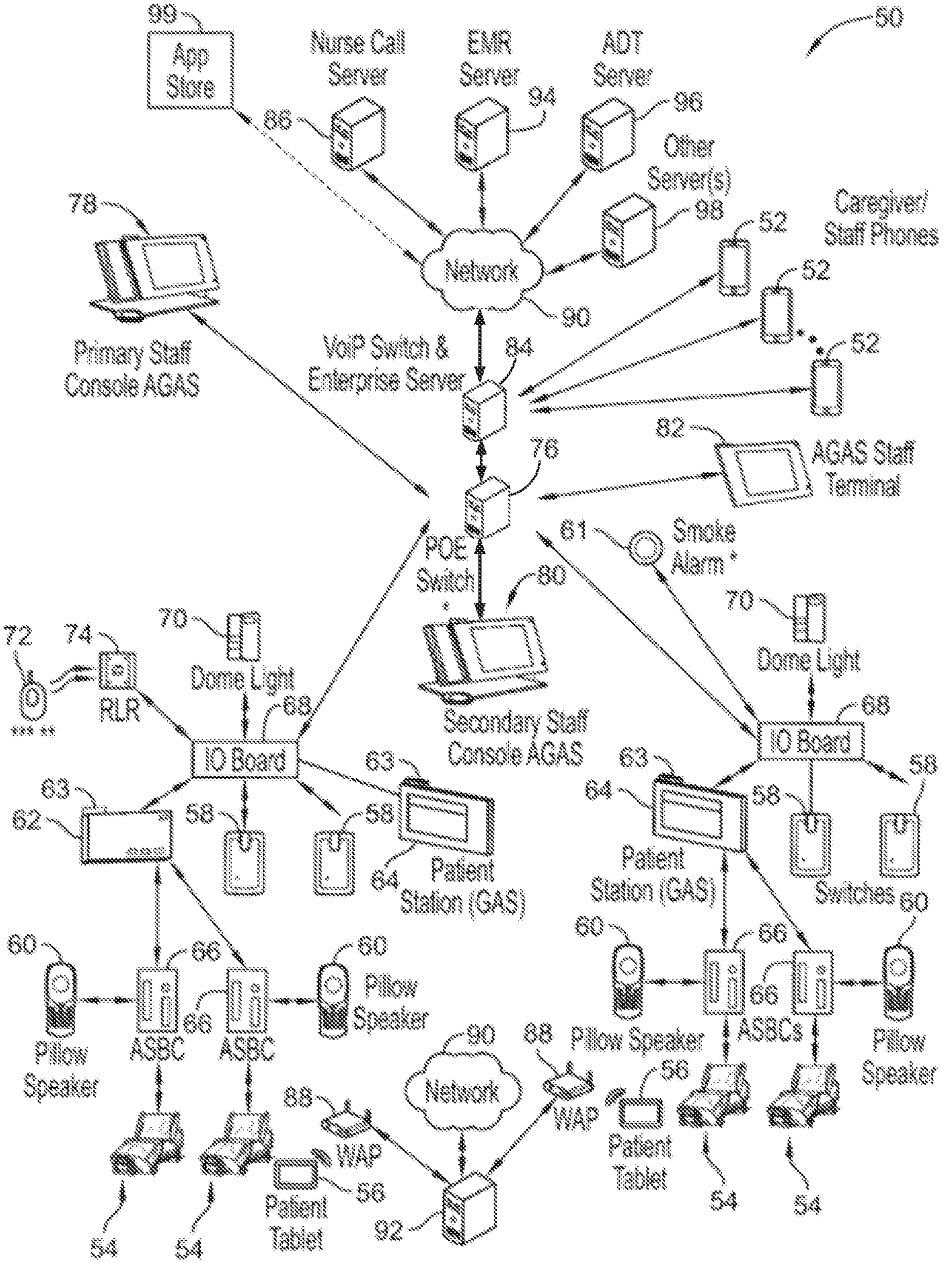
FIG. 1 is a schematic diagram of a caregiver communications system that includes a plurality of mobile devices each equipped with a mobile caregiver application for managing messages between caregivers in a healthcare facility.

FIG. 1 is a schematic diagram of a caregiver communications system 50 in a healthcare facility such as a hospital, clinic, nursing home, and the like. The caregiver communications system 50 includes a number of mobile devices 52 that operate a mobile caregiver application 200 (shown in FIG. 2) for managing messages between caregivers in the healthcare facility, and calls and alerts originating from assigned patients and various hospital equipment associated with the assigned patients in the healthcare facility.

The caregiver communications system 50 can be part of a hospital information system (HIS), which focuses on the administrational needs of the healthcare facility. As an illustrative example, the HIS is a comprehensive, integrated information system for managing all the aspects of the healthcare facility's operation, such as medical, administrative, financial, and legal issues and the corresponding processing of services. In certain aspects, the caregiver communications system 50 can share similar aspects with the system described in U.S. patent application Ser. No. 16/143,971, titled CAREGIVER AND STAFF INFORMATION SYSTEM, filed on Sep. 27, 2018, the entirety of which is hereby incorporated by reference.

The mobile caregiver application 200 allows caregivers and staff to use their mobile devices 52 to conduct voice, video, and text messaging between themselves, monitor alerts and calls from assigned patients, and permit voice communications to audio stations 62, 64 mounted in patient rooms adjacent to respective patient beds 54. In some examples, the mobile devices 52 are smartphones, tablet computers, or similar devices. The mobile caregiver application 200 can act as a secondary notification system that supplements a nurse call server 86 of the caregiver communications system 50 that will be described in more detail below.

The calls and alerts from assigned patients and various hospital equipment may originate from the patient beds 54, patient tablets 56, call switches 58, and pillow speaker units 60. Alerts may also originate from a smoke alarm 61. In some examples, the audio stations 62, 64 can include a code blue call lever 63 which can be pulled by a caregiver in an emergency such as when a patient is having a medical emergency such as a heart attack. In the example of FIG. 1, the pillow speaker units 60 of the patient beds 54 are coupled to the audio stations 62, 64 by audio station bed connectors (ASBCs) 66. Alternatively, one or more network interface units (NIUs) or wireless interface units (WIUs) can provide the connectivity between the patient beds 54 and respective audio stations 62, 64 instead of the ASBCs 66.

The call switches 58, smoke alarm 61, and audio stations 62, 64 are each communicatively coupled to a respective input/output (I/O) circuit board 68. Each circuit board 68 includes a processor, such as a microprocessor, microcontroller, and the like that receives various alerts and calls, sometimes referred to herein as "alert messages," from the patient beds 54, pillow speaker units 60, smoke alarms 61, and audio stations 62, 64. The processor of each circuit board 68 determines an alert message priority designation for each of the incoming alert messages. For example, alert messages can be designated as normal alert messages or high priority alert messages. Additional types of message priority designations may also be used.

Each circuit board 68 is coupled to a respective dome light 70 which can include multiple lights that are illuminated to indicate a room status. The illumination of the dome light 70 is controlled by the circuit board 68 based on alert conditions occurring in the respective patient room and based on caregiver presence in, or absence from, the patient room. Dome lights 70 are mounted outside each patient room, typically near a doorway to the respective room. In some examples, circuit board 68 are installed in a housing to which the dome lights 70 are mounted. Thus, the circuit board 68 can be located outside the patient rooms adjacent the dome lights 70. Alternatively, the circuit board 68 can be located inside the patient rooms. In either case, the circuit board 68 are considered to be "at" the patient room according to this disclosure.

A locating badge 72 is shown in wireless communication with a remote locator receiver (RLR) 74 which, in turn, is communicatively coupled with the circuit board 68 in the respective patient room in which the RLR 74 is located. The caregiver communications system 50 can include multiple locating badges 72 each worn by a respective caregiver, and multiple RLRs located throughout the healthcare facility. In response to an RLR 74 detecting one or more locating badges 72 in any particular room, a signal or message is communicated to the respective circuit board 68 and the lighting of the dome light 70 is updated accordingly to indicate the presence of a caregiver in the patient room. In certain examples, the locating badges 72 transmit infrared (IR) signals to RLRs 74. Alternative examples are also possible in which radio frequency (RF) transmissions, including ultra-wideband (UWB) transmissions, are made by the locating badges 72 to the RLRs 74 that are in the patient rooms.

Still referring to FIG. 1, each circuit board 68 is communicatively coupled to a Power over Ethernet (PoE) switch 76 which is, in turn, communicatively coupled to a primary staff console 78 (sometimes referred to as a "master nurse station"), a secondary staff console 80, and a staff terminal 82. PoE switch 76 is communicatively coupled to a voice over Internet protocol (VoIP) Switch and Enterprise server 84 which is, in turn, coupled to a nurse call server 86 via Ethernet infrastructure, illustrated diagrammatically as network 90 in FIG. 1. Also, the mobile devices 52 are communicatively coupled to the VoIP Switch and Enterprise server 84, which can provide access on the mobile devices

52 to an electronic medical records (EMR) server 94, an admission, discharge, transfer (ADT) server 96, and additional servers 98 via the network 90.

The network 90 can include any type of wired or wireless connections or any combinations thereof. Examples of wired connections include fiber optic, ethernet, and other wired computer networking technologies. Examples of wireless connections include broadband cellular networks such as 4G and 5G, Wi-Fi, Bluetooth, and the like.

The call switches 58, pillow speaker units 60, audio stations 62, 64, ASBC's 66, circuit board 68, dome light 70, PoE switch 76, primary staff console 78, secondary staff console 80, staff terminal 82, VoIP Switch and Enterprise server 84, and nurse call server 86 are illustrative of a diagrammatic nurse call system portion of the caregiver communications system 50 and that nurse call system architecture will vary from one healthcare facility to the next.

The patient tablets 56 can also be included as part of the nurse call system portion of the caregiver communications system 50. The patient tablets 56 are used by patients to send requests such as requests for pain medication, requests for bathroom assistance, food requests, drink requests, ice chips requests, requests for assistance with personal care, and the like. In the illustrative example, the patient tablets 56 communicate wirelessly with wireless access points (WAP) 88 which, in turn, communicate with a patient tablet communications server 92. The patient tablet communications server 92 communicates the patient requests, which are also considered to be alert messages, to the nurse call server 86 via the network 90.

The alert messages originating from the patient beds 54 can include alert messages relating to a bed exit of the patient from a patient bed 54, patient position on a patient bed 54 exceeding a threshold, patient movement on a patient bed 54 exceeding a threshold or falling below a threshold, siderail position (e.g., siderail down) of a patient bed 54, casters of a patient bed 54 not being braked, angle of a head section of a patient bed 54 being below a threshold angle (e.g., 30 degrees), an upper frame of a patient bed 54 not being in its lowest position relative to a base frame of the patient bed 54, a bed component of a patient bed 54 exceeding a threshold temperature, a mattress bladder of a patient bed 54 falling below a threshold pressure, a pneumatic system error or failure of a patient bed 54, an actuator error or failure of a patient bed 54, an overcurrent condition of a component of a patient bed 54, a power system error or failure of a patient bed 54, and power disconnection from a patient bed 54.

As shown in FIG. 1, the caregiver communications system 50 includes the electronic medical records (EMR) server 94 and the admission, discharge, transfer (ADT) server 96. The EMR server 94 and the ADT server 96 can be part of the HIS.

The EMR server 94 stores electronic medical/health records for each patient admitted to the healthcare facility. These records can be shared across the HIS, and other information networks and exchanges, including the various components of the caregiver communications system 50. For example, these records can be shared through the network 90. The electronic medical/health records include a range of data, such as medical history, medication and allergies, immunization status, laboratory test results, radiology images, vital signs, and personal statistics like age and weight, and billing information for each patient admitted to the healthcare facility.

The ADT server 96 is used by the caregiver communications system 50 to track the location and status of patients from their arrival until their departure from the healthcare facility including events such as when a patient is transferred to a new department, unit, or room within the healthcare facility. The ADT server 96 stores information for each patient admitted to the healthcare facility such as the patient's medical record number, name, age, sex, contact information, date of admission, reason for admission, and the like. The patient information within the ADT server 96 can be shared with other components of the caregiver communications system 50 including the hospital information system, as will be described in more detail.

The caregiver communications system 50 may also include additional servers 98. The nurse call server 86, EMR server 94, ADT server 96, and additional servers 98 are accessible on the mobile devices 52 via the VoIP Switch and Enterprise server 84 and network 90.

In certain examples, the additional servers 98 can include, for example, a real time locating system (RTLS) server that is communicatively coupled to RLRs 74. In such examples, the locating badges 72, RLRs 74, and RTLS server form a real time locating system portion of the caregiver communications system 50. Staff locating information can be communicated from the RTLS server to the nurse call server 86 via the network 90.

In some examples, the additional servers 98 can include a server that manages the routing of alert messages and related staff information to the mobile device 52. In general, alert messages relating to particular patients or particular rooms assigned to particular caregivers are sent to the mobile device 52 of that particular caregiver. The alert messages may originate from the patient beds 54, pillow speaker units 60, and patient tablets 56. Additionally, it is also possible that alert messages originating from other types of equipment may be communicated to the mobile devices 52 of assigned caregivers as well.

The features and functions of the mobile caregiver application 200 are described below in more detail with reference to FIGS. 2-25 that include various screen shots that can appear on the mobile devices 52. By seeing the functionality represented in each of the screen shots and by considering the following description of the screen shots of FIGS. 2-25, those skilled in the art will be enabled to make and use the mobile caregiver application 200, and its variant embodiments, contemplated herein. It should be appreciated that the screen shots of this disclosure are exemplary in nature and are provided to give a general sense of the type of information that may appear on a display screen of any given mobile device 52 during use of the mobile caregiver application 200 by the caregivers. Thus, the screen shots are merely individual examples from a practically unlimited number of possibilities. That is, the information such as alert messages, staff names, staff locations, room name formats, unit names, and the like may vary from healthcare facility to healthcare facility and may vary in any given healthcare facility throughout any given day in response to the various incoming alert messages, for example.

Figure 2:
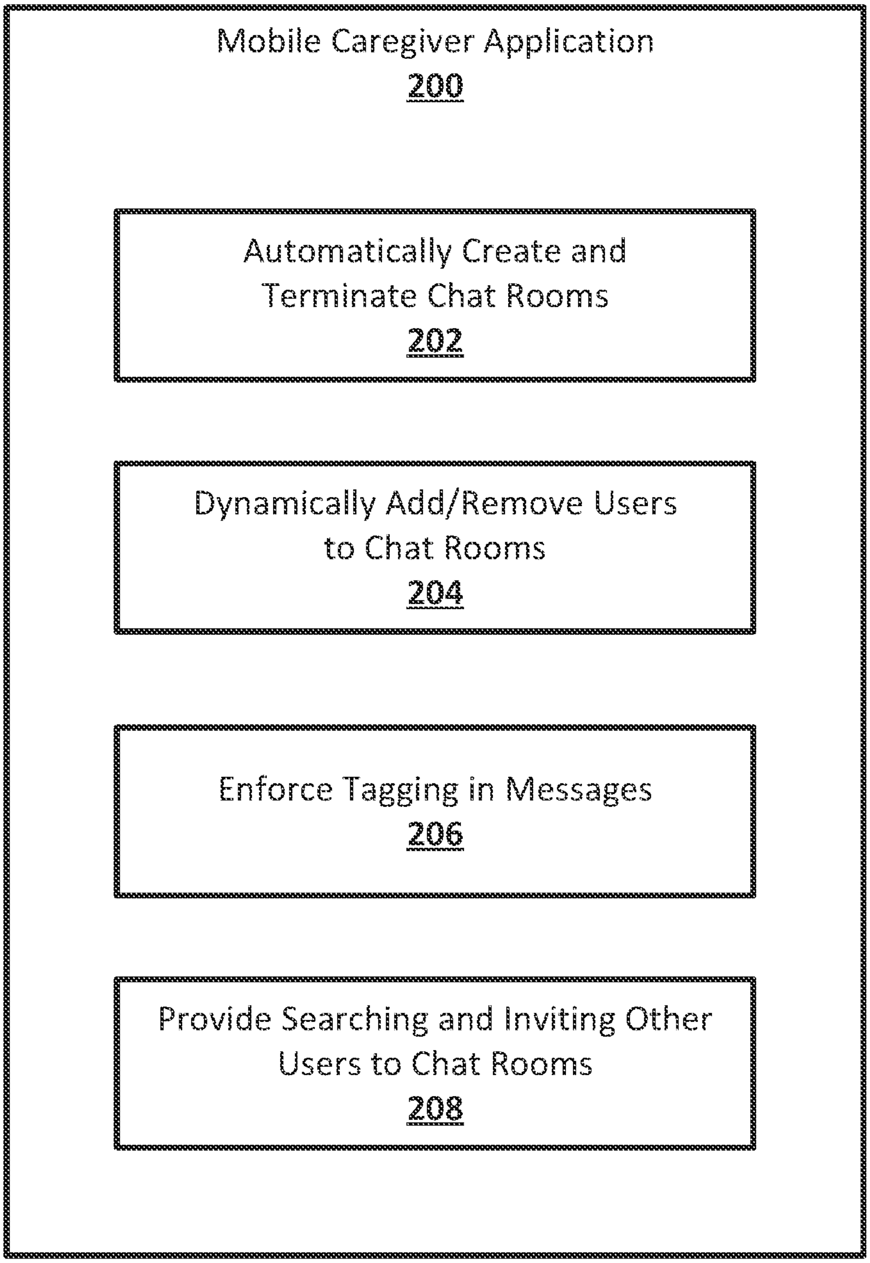
FIG. 2 schematically illustrates the mobile caregiver application.

FIG. 2 schematically illustrates the mobile caregiver application 200. The mobile caregiver application 200 is operated on the mobile devices 52 of the caregivers. The mobile caregiver application 200 can also be operated on one or more servers connected to the network 90 such as the nurse call server 86, EMR server 94, ADT server 96, and additional servers 98.

The mobile caregiver application 200 is available for downloading on the mobile device 52 from an App Store 99 (see FIG. 1) accessible via the Internet. Alternatively, the mobile caregiver application 200 can also be downloaded on the mobile devices 52 by connecting the mobile devices to a data storage device that has the mobile caregiver application 200 stored thereon. In some examples, the mobile caregiver application 200 is downloaded onto the mobile devices 52 under the supervision and authorization of an administrator.

As shown in the example depicted in FIG. 2, the mobile caregiver application 200 includes a software module 202 to automatically create and terminate chat rooms, a software module 204 to dynamically add and remove caregivers to the chat rooms, a software module 206 to enforce tagging in messages sent in the chat rooms, and a software module 208 to enable searching and inviting other caregivers to the chat rooms. The mobile caregiver application 200 may include fewer or additional software modules as desirable such that the software modules 202-208 shown in FIG. 2 are provided for illustrative purposes only.

In certain embodiments, the mobile caregiver application 200 is used to create and manage patient-centric chat rooms that are centralized around a patient admitted to the healthcare facility. Additionally, the mobile caregiver application 200 is used to create and manage shift-centric chat rooms such as for departments, units, and teams within a healthcare facility.

Figure 3:
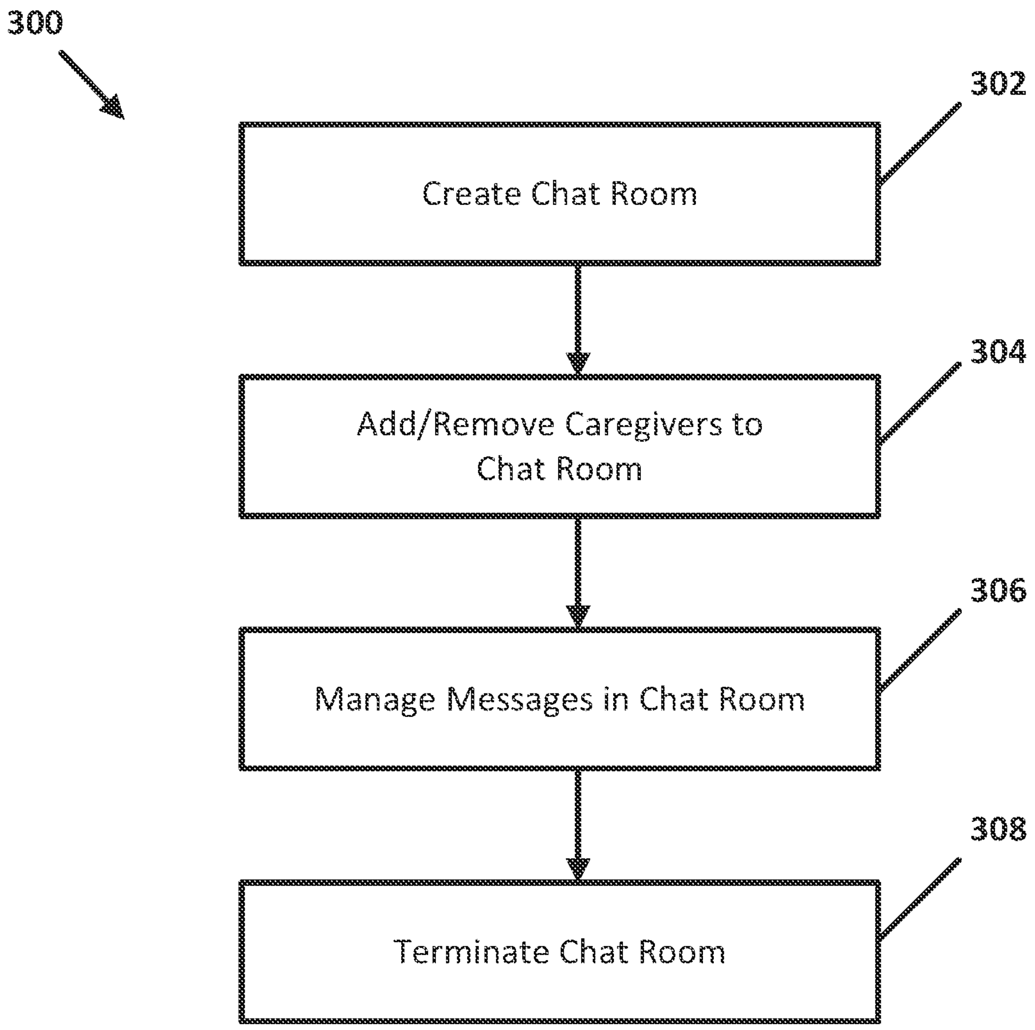
FIG. 3 illustrates an example of a method of managing messages between caregivers on the mobile devices of the caregiver communications system of FIG. 1.

FIG. 3 illustrates an example of a method 300 of managing messages between caregivers on the mobile devices 52. The method 300 is directed to creating and managing patient-centric chat rooms which, as described above, are centralized around a patient.

The method 300 is performed by the mobile caregiver application 200, and utilizes the infrastructure of the caregiver communications system 50 to enable caregivers to quickly communicate with one another. The patient-centric chat rooms allow caregivers assigned to a patient to communicate with one another at any given time. Unlike normal group messages, the patient-centric chat rooms are dynamically updated based on the assignment of the caregivers to the patient. Advantageously, the patient-centric chat room can prevent the loss of information, comments, and details that are not typically entered into a patient's medical record.

The method 300 includes an operation 302 of creating a chat room, an operation 304 of dynamically adding and removing caregivers to the chat room, an operation 306 of managing messages in the chat room, and an operation 308 of terminating the chat room.

Figure 4:
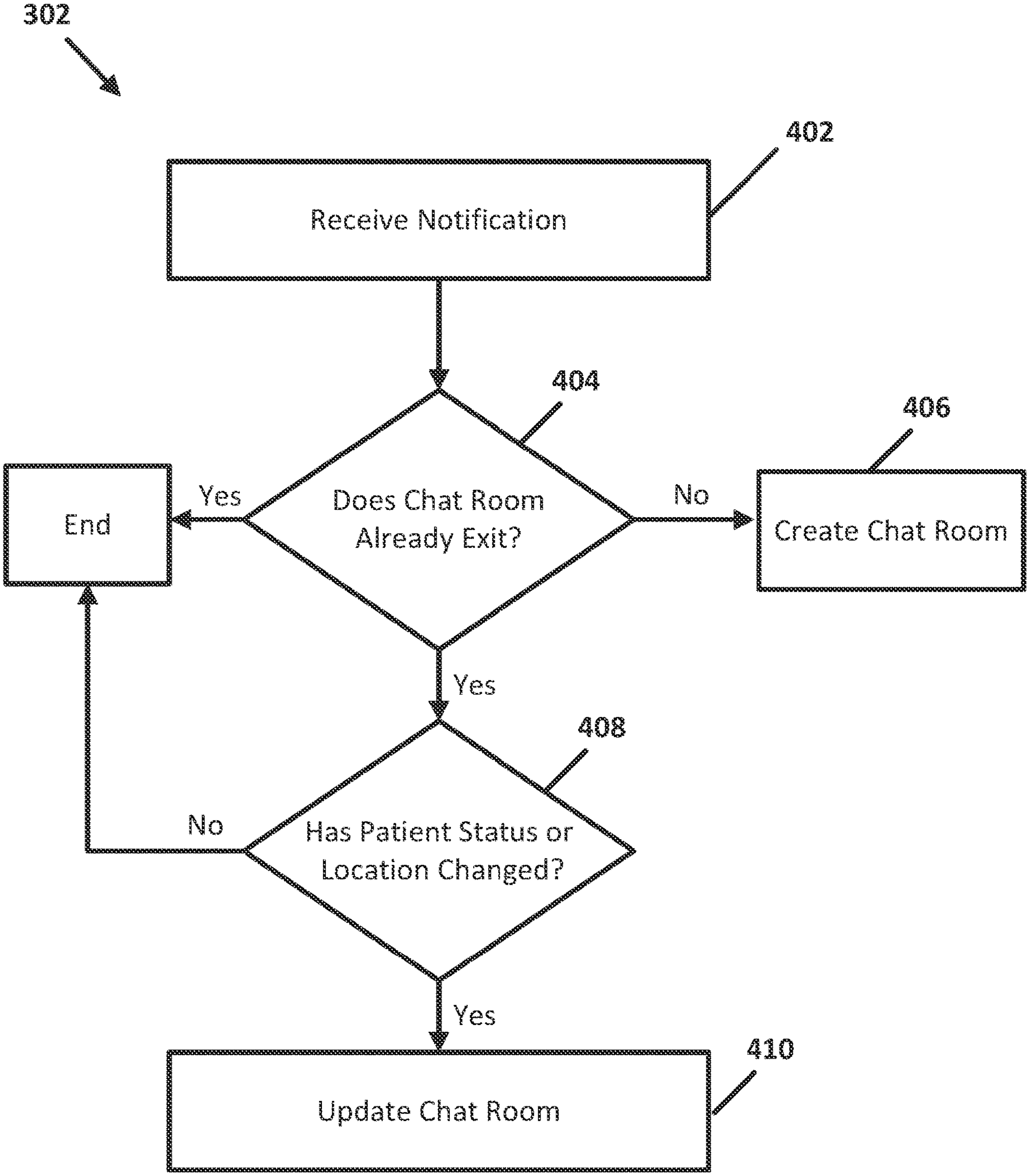
FIG. 4 illustrates an operation of the method of FIG. 3 in more detail to create a patient-centric chat room.

FIG. 4 illustrates operation 302 in more detail which is performed by the software module 202 of the mobile caregiver application 200 to create a patient-centric chat room for a patient that is newly admitted to the healthcare facility. The patient-centric chat room is automatically created without requiring any input or action from the caregivers. Advantageously, the caregivers can begin to receive messages on their mobile device 52 from the patient-centric chat room for the given patient once the patient is admitted to the healthcare facility.

Referring now to FIG. 4, operation 302 includes a step 402 of receiving a notification identifying a patient admitted to the healthcare facility. The notification can be received by the mobile caregiver application 200 from the ADT server 96 such as through the network 90. The notification can be received at the time the patient is admitted to the healthcare facility.

The notification can include at least the patient's name, and room number or department or unit within the healthcare facility. Additionally, the notification can include additional information acquired from the ADT server 96 including the patient's medical record number, age, sex, date of admission, reason for admission, and the like.

Next, operation 302 includes a step 404 of determining whether a patient-centric chat room for the patient already exists. When it is determined that a patient-centric chat room for the patient does not already exist (i.e., "No" at step 404), operation 302 proceeds to a step 406 of creating the patient-centric chat room for the newly admitted patient.

When it is determined that a patient-centric chat room for the patient already exists (i.e., "Yes" at step 404), operation 302 ends. Alternatively, when it is determined that a patient-centric chat room for the patient already exists (i.e., "Yes" at step 404), operation 302 can proceed to a step 408 of determining based on the notification received from the ADT server 96 whether the patient's status or location has changed. When it is determined that the patient's status or location has not changed (i.e., "No" at step 408), operation 302 ends.

When it is determined that the patient's status or location has changed (i.e., "Yes at step 408), operation 302 proceeds to a step 410 of updating the patient-centric chat room based on the changed status or location of the patient as determined from the notification received from the ADT server 96. For example, the patient-centric chat room can be updated when the patient is transferred to a new room or department or unit within the healthcare facility.

Figure 5:
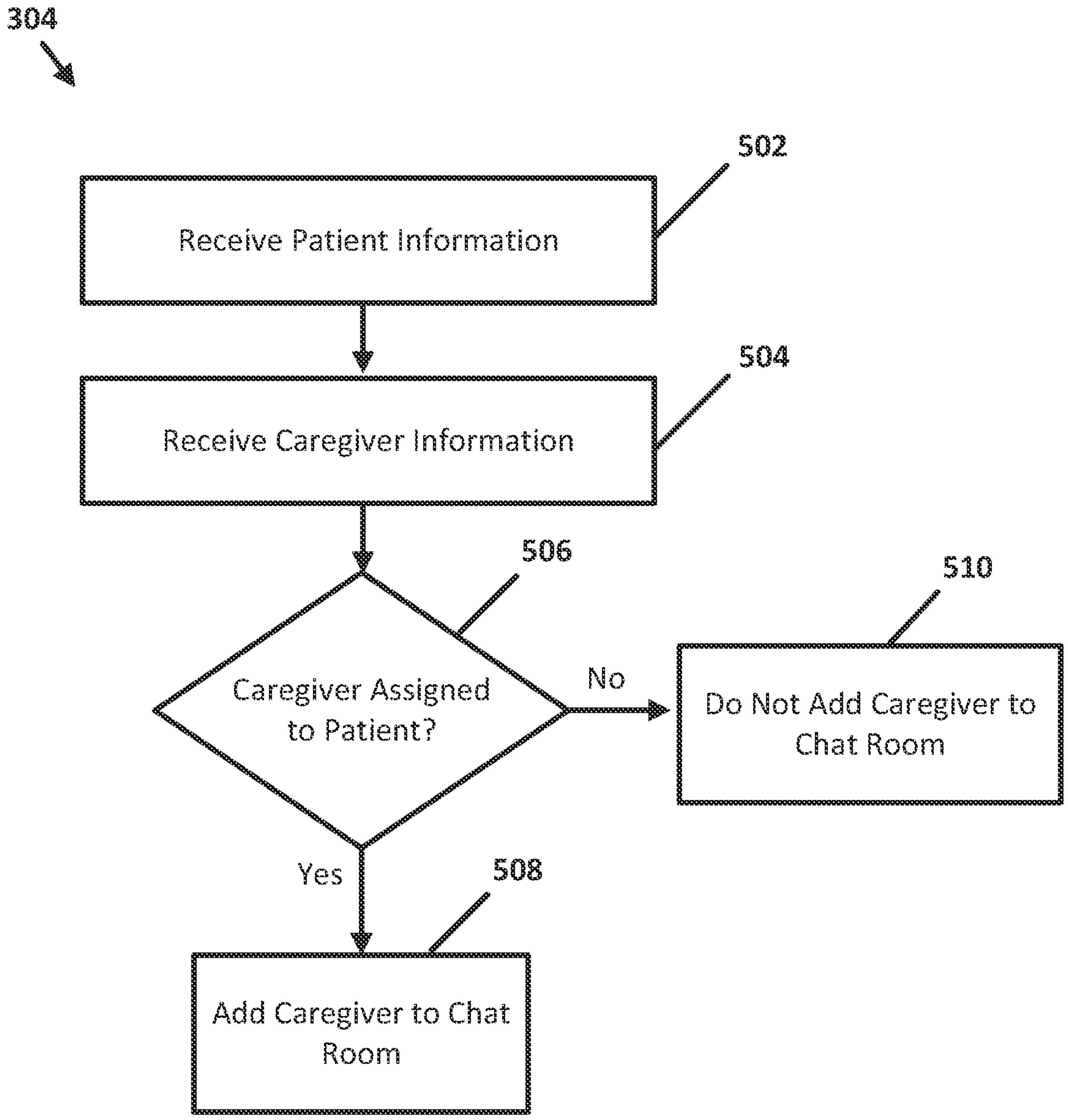
FIG. 5 illustrates an operation of the method of FIG. 3 in more detail to assign caregivers to the patient-centric chat room.

FIG. 5 illustrates operation 304 in more detail which is performed by the software module 204 of the mobile caregiver application 200 to dynamically add and remove caregivers to the patient-centric chat room. The software module 204 dynamically updates the patient-centric chat rooms on the mobile device 52 by communicating with the nurse call server 86, EMR server 94, ADT server 96, and/or additional servers 98 via the network 90 and VoIP Switch and Enterprise server 84. Referring now to FIG. 5, operation 304 includes a step 502 of receiving patient information such as the patient's name or ID number, and the patient's room number or unit within the healthcare facility. The patient information can be acquired from the EMR server 94, ADT server 96, and additional servers 98, and is monitored and continuously updated.

Next, operation 304 includes a step 504 of receiving caregiver information. The caregiver information can be received by the mobile caregiver application 200 from the caregiver communications system 50 via the network 90. For example, the caregiver information can be received from any one of the nurse call server 86, the primary and secondary staff consoles 78, 80, the staff terminal 82, or the additional servers 98.

The caregiver information identifies caregivers based on (1) their assignment to patients, or (2) their assignment to one or more rooms or departments or units within the healthcare facility. The caregiver information also identifies the status of caregivers such as whether they are on shift or off shift. The caregiver information is monitored and continuously updated by the nurse call server 86, the primary and secondary staff consoles 78, 80, the staff terminal 82, or the additional servers 98.

Next, operation 304 includes a step 506 of determining whether a caregiver is assigned to the patient. A caregiver is assigned to the patient when the caregiver has a role that provides patient viewing privileges and at least one of the following assignments: (1) EMR assignment to the patient; (2) manual assignment to the patient; and (3) room-based or unit-based assignment to the patient. When it is determined that a caregiver is assigned to the patient (i.e., "Yes" at step 506), operation 304 proceeds to a step 508 of adding the caregiver to the patient-centric chat room. In some instances, when the caregiver is already a member of a patient-centric chat room for a given patient, step 508 can include confirming and/or maintaining the caregiver's membership to the patient-centric chat room. Additionally, step 508 ensures that only caregivers with patient viewing privileges are added to the patient-centric chat room which helps to maintain the privacy of the information communicated in the chat room, and compliance with the Health Insurance Portability and Accountability Act (HIPAA).

When it is determined that a caregiver is not assigned to the patient (i.e., "No" at step 506), operation 304 does not add the caregiver to the patient-centric chat room at step 510. When the caregiver is a member of a patient-centric chat room for a given patient, step 510 can include removing the caregiver from the patient-centric chat room. Steps 502-510 can be repeated such that the membership of the caregivers to the patient-centric chat room is continuously updated while the patient remains admitted in the healthcare facility.

In view of the foregoing, a caregiver is added to a patient-centric chat room based on (1) their assignment directly to a patient, or (2) their assignment to a location associated with the patient such as the patient's room or unit within the healthcare facility.

Unlike typical group messaging, the assignment of caregivers to the patient-centric chat rooms is dynamically updated based on the location and status of a patient within the healthcare facility. For example, when the patient is transferred to a new room, the patient-centric chat room for the patient is dynamically updated by the software module 204 to add caregivers based on the new room of the patient, and to remove caregivers that were assigned to the patient-centric chat room based on the patient's previous room. Thus, a caregiver can lose their membership to a patient-centric chat room when the caregiver loses their assignment to the patient or their patient viewing privileges, or the patient is transferred to another room where the caregiver is not assigned, or when the patient is discharged from the healthcare facility.

When a caregiver loses patient viewing privileges, all of the patient related information, including the patient-centric chat room, will no longer be accessible on the mobile device 52 of the caregiver. In some example, the patient-centric chat room displays a banner to notify the caregiver that they no longer have access to the chat room because the patient has been transferred to another room or has been discharged from the healthcare facility.

The removal of a caregiver from a patient-centric chat room is based on how the caregiver was added to the chat room. As an illustrative example, a caregiver can remain a member of the patient-centric chat room when the caregiver was added to the patient-centric chat room based on an EMR assignment to the patient, even though the patient has been transferred to another room. However, when a message from the EMR server 94 indicates that the caregiver is no longer assigned to the patient, the caregiver is removed from the patient-centric chat room.

In examples where a caregiver is added to a patient-centric chat room based on a manual assignment to the patient, the caregiver is removed from the patient-centric chat room when the caregiver is manually unassigned from the patient. In examples where a caregiver is added to a patient-centric chat room based their assignment to the patient's room, the caregiver is removed from the patient-centric chat room when a message from the ADT server 96 indicates that the patient has been moved to a different room where the caregiver is not assigned, or where the caregiver does not have patient viewing privileges.

Membership to the patient-centric chat room is also dynamically updated based on the caregiver's status. For example, when a caregiver ends their shift, the patient-centric chat room can be dynamically updated to remove the caregiver such that the caregiver no longer receives messages on their mobile device 52 from the patient-centric chat room. When the caregiver starts their shift and they are assigned to a patient or patient room, a patient-centric chat room associated with the patient or patient room number is dynamically updated to add the caregiver as a member so that the caregiver can immediately begin to receive messages on their mobile device 52 from the patient-centric chat room. The caregiver can be added to the patient-centric chat room without requiring any input or action from the caregiver.

Referring now to FIG. 3, operation 306 of managing messages in the chat room includes providing features to enhance communication between caregivers in the patient-centric chat room. These features can include providing the ability for a caregiver to tag another caregiver in a message to ensure that the message is seen by an intended caregiver. Also, the features include enabling a caregiver to search and invite one or more additional caregivers to the patient-centric chat room that are not assigned to the patient or the patient's location. These features will be described in more detail below. Similar features can also be provided in the shift-centric chat rooms that are described in more detail below. Operation 306 is performed by the software modules 206, 208 of the mobile caregiver application 200.

Figure 6:
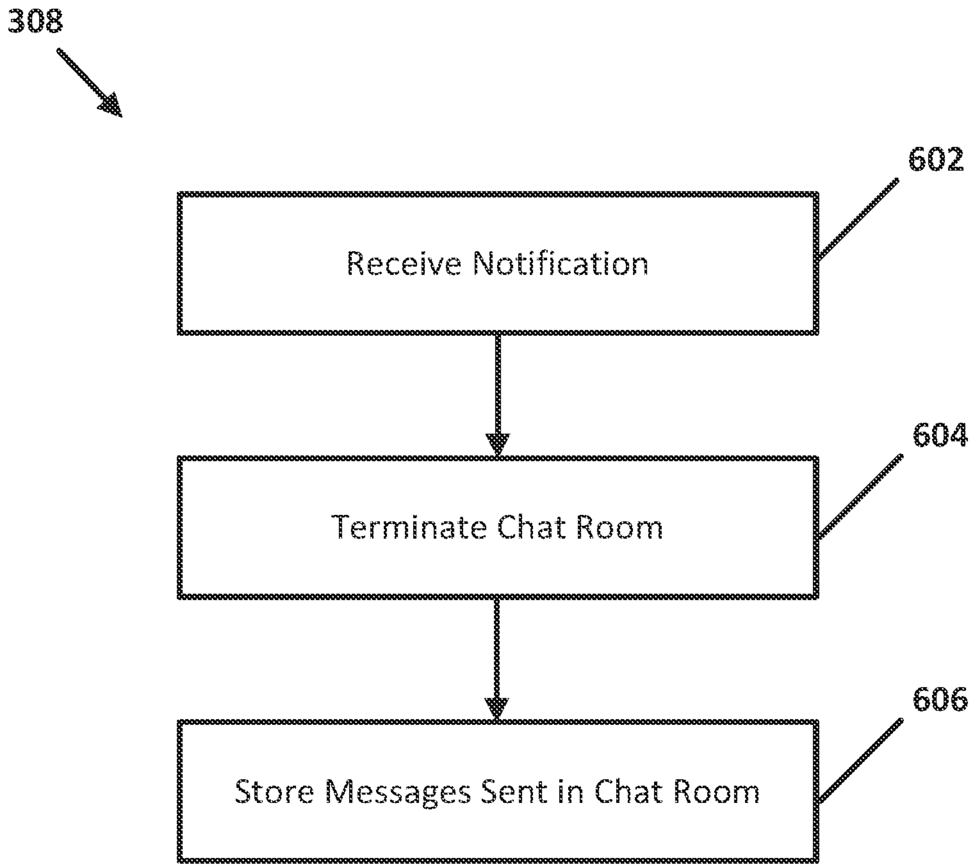
FIG. 6 illustrates an operation of the method of FIG. 3 in more detail to terminate the patient-centric chat room after the patient is discharged from the healthcare facility.

FIG. 6 illustrates operation 308 of the method 300 in more detail. Operation 308 is performed by the software module 202 of the mobile caregiver application 200 to terminate the patient-centric chat room after the patient is discharged from the healthcare facility. Referring now to FIG. 6, operation 308 includes a step 602 of receiving a notification that the patient has been discharged from the healthcare facility. The notification can be received by the mobile caregiver application 200 from the ADT server 96 such as through the network 90.

After receiving the notification that the patient has been discharged, operation 308 proceeds to step 604 of terminating the patient-centric chat room. Thus, the patient-centric chat room persists until the patient is discharged from the healthcare facility. In some examples, the patient-centric chat room is automatically terminated without requiring any input or action from the caregivers. Accordingly, the caregivers cease to receive messages from the patient-centric chat room on their mobile device after the patient is discharged from the healthcare facility. In certain examples, the patient-centric chat room displays a banner notifying the caregivers that the patient has been discharged and they no longer have access to the patient's chat room. At least one technical advantage of automatically terminating the patient-centric chat room is the reduction of storage requirements on the mobile devices of the caregivers.

In some examples, operation 308 includes a step 606 of storing the messages sent in the patient-centric chat room to a file that can be later accessed and reviewed after the patient's discharge. Advantageously, the messages sent in the patient-centric chat room can be reviewed for compliance with healthcare protocols and/or parsed for information that is typically not recorded in the patient's medical record to improve patient care.

In certain examples, the messages sent in the patient-centric chat room are stored in the EMR server 94. For example, the mobile caregiver application 200 can utilize VoIP Switch and Enterprise server 84 and network 90 (shown in FIG. 1) to communicatively couple the mobile devices 52 to the EMR server 94 such that the messages sent in the patient-centric chat room are saved to the patient's medical record in the EMR server 94.

Figure 7:
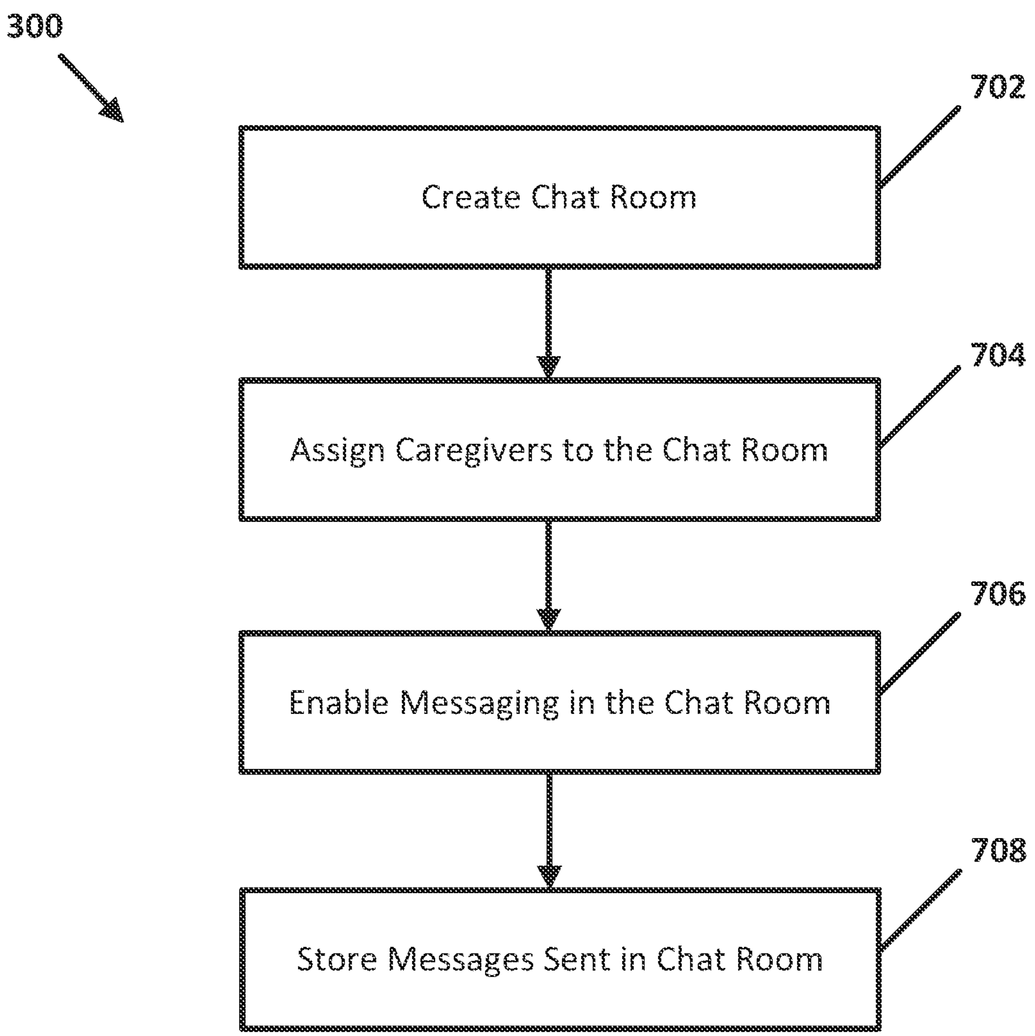
FIG. 7 illustrates another example of a method of managing messages between caregivers on the mobile devices of the caregiver communications system of FIG. 1.

FIG. 7 illustrates an example of a method 700 of managing messages between caregivers on the mobile devices 52. The method 700 is directed to creating and managing shift-centric chat rooms. The method 700 is performed by the mobile caregiver application 200, and utilizes the infrastructure of the caregiver communications system 50 to enable caregivers to quickly communicate with one another in shift-centric chat rooms. Advantageously, the method 700 can help maintain a history of caregiver communications across caregiver shifts.

Referring now to FIG. 7, the method 700 includes an operation 702 of automatically creating a chat room, an operation 704 of assigning caregivers to the chat room, and an operation 706 of enabling messaging in the chat room, and an operation 708 of storing the messages sent in the shift-centric chat room. Unlike the method 300 described above, the method 700 does not terminate the chat room because the shift-centric chat rooms persist indefinitely since they are based on a department, unit, or team within the healthcare facility.

Operation 702 includes creating a chat room for a department, unit, or team within the healthcare facility such as, without limitation, an emergency department, an intensive care unit, a trauma center, a neonatal intensive care unit, a surgical unit, a burn unit, rapid response teams, a cardiology department, and the like. Operation 702 can be performed by the software module 202 of the mobile caregiver application 200 to create the shift-centric chat room.

Operation 704 can include receiving information from one or more of the nurse call server 86, the primary and secondary staff consoles 78, 80, and the staff terminal 82 to determine which caregivers are assigned to the designated department, unit, or team of the shift-centric chat room. Based on this information, the caregivers are added to the chat room at operation 704. Also, caregivers can be dynamically added to shift-centric chat rooms when they assign themselves to a department, team, or unit in the caregiver communications system 50.

Additionally, operation 704 can also include determining whether the caregivers assigned to the designated department, unit, or team are on shift or off shift. This information is monitored and continuously updated based on the data received from the nurse call server 86 and/or the primary and secondary staff consoles 78, 80, and/or the staff terminal 82. Thus, the caregivers are added to one or more shift-centric chat rooms when they begin their shift and the caregivers are removed from the shift-centric chat rooms when they end their shift.

Advantageously, messages from shift-centric chat rooms can be blocked on the mobile devices 52 of the caregivers when the caregivers are off shift, such as when they are at home off from work. Also, the caregivers when on shift can automatically receive messages from the shift-centric chat rooms on their mobile devices 52 without requiring any input or action from the caregivers. In some examples, caregivers are removed from a shift-centric chat room when they manually remove themselves from a unit or team by editing their shift. Also, caregivers can be removed from shift-centric chat rooms when an assignment bump removes them from an exclusive role that causes the caregiver to no longer be part of a unit or team.

Operation 706 of enabling messaging in the chat room includes providing features to enhance communication between caregivers in the shift-centric chat room. These features are similar to the features described above with respect to operation 306 of the patient-centric chat rooms, and will be described in more detail below with reference to FIGS. 9-25. Operation 706 is performed by the software modules 206, 208 of the mobile caregiver application 200.

Operation 708 includes storing the messages sent in the shift-centric chat room to a memory that can be later accessed and reviewed. Advantageously, the messages sent in the shift-centric chat room can be reviewed for compliance with healthcare protocols and/or parsed for information that is typically not recorded in medical records to improve patient care.

In certain examples, the messages sent in the patient-centric chat room are stored in at least one of the nurse call server 86, EMR server 94, ADT server 96, or additional servers 98. For example, the mobile caregiver application 200 can utilize VoIP Switch and Enterprise server 84 and network 90 (shown in FIG. 1) to communicatively couple the mobile devices 52 to the nurse call server 86, EMR server 94, ADT server 96, or additional servers 98 such that the messages sent in the shift-centric chat rooms can be sent to the nurse call server 86, EMR server 94, ADT server 96, or additional servers 98 for storage. In certain examples, the messages from the shift-centric chat rooms are destroyed after a predetermined amount of time has elapsed.

Figure 8:
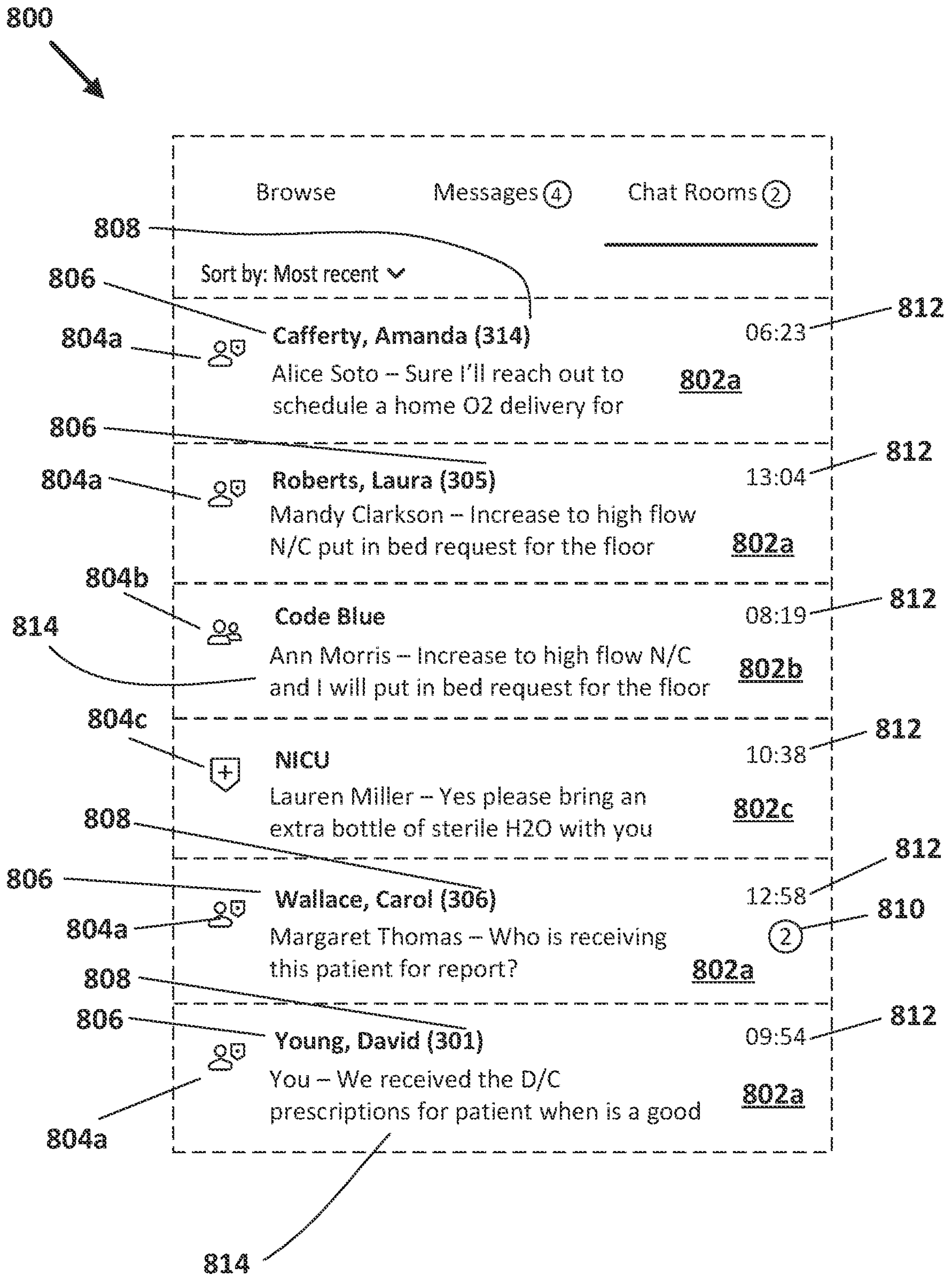
FIG. 8 shows an example of a chat room tab that can be displayed on the mobile device of a caregiver to provide access to patient-centric and shift-centric chat rooms.

FIG. 8 shows an example of a chat rooms tab 800 displayed by the mobile caregiver application 200 on a mobile device 52 of a caregiver. Once a caregiver is assigned to a patient-centric chat room or shift-centric chat room, the chat rooms are accessible by the caregiver from the chat rooms tab 800. As shown in FIG. 8, a plurality of chat rooms 802 to which the caregiver is assigned are displayed in a single list on the chat rooms tab 800. In certain examples, the plurality of chat rooms 802 can be sorted by ordering the chat rooms 802 based on which ones have most recently received a message, relevancy, or some other metric.

As shown in FIG. 8, different types of chat rooms are displayed in the single list on the chat rooms tab 800. For example, chat rooms 802*a* are patient-centric chat rooms, while chat room 802*b* is a shift-centric chat room for a code blue team within the healthcare facility, and chat room 802*c* is a shift-centric chat room for a neonatal intensive care unit (NICU) within the healthcare facility. Additional types of chat rooms can be included on the chat rooms tab 800.

The chat rooms tab 800 identifies the different types of chat rooms by providing symbols 804 next to each chat room 802. For example, a first type of symbol 804*a* can be used to identify the chat rooms 802*a* that are patient centric, a second type of symbol 804*b* can be used to identify the chat rooms 802*b* that are shift-centric and dedicated to a team within the healthcare facility, and a third type of symbol 804*c* can be used to identify the chat rooms 802*c* that are shift-centric and dedicated to a unit or department within the healthcare facility.

For each chat room 802*a* that is patient-centric, the chat rooms tab 800 identifies the patent's name 806, and the patient's room number 808. The chat rooms tab 800 can also display the name of the team, unit, or department for the shift-centric chat rooms 802*b*, 802*c*.

The chat rooms tab 800 can provide symbols 810 that identify unread messages within each chat room 802*a*. In some examples, the symbols 810 identify a quantity of unread messages. Additionally, the chat rooms tab 800 may also provide a time stamp 812 that identifies the last time a message was received in a particular chat room 802. Also, the chat rooms tab 800 may also provide at least a portion 814 of the last message received in each chat room 802.

In addition to the chat rooms tab 800, a patient-centric chat room can also be accessed by a caregiver from a patient record that includes a chat tab to show the recorded contents of the patient-centric chat room. The patient record and chat tab can be displayed on the primary or secondary staff consoles 78, 80, the staff terminal 82, or on the mobile devices 52. In certain examples, the patient record is an electronic medical record (EMR) or electronic health record (EHR) that is stored on the EMR server 94 shown in FIG. 1.

Figure 9:
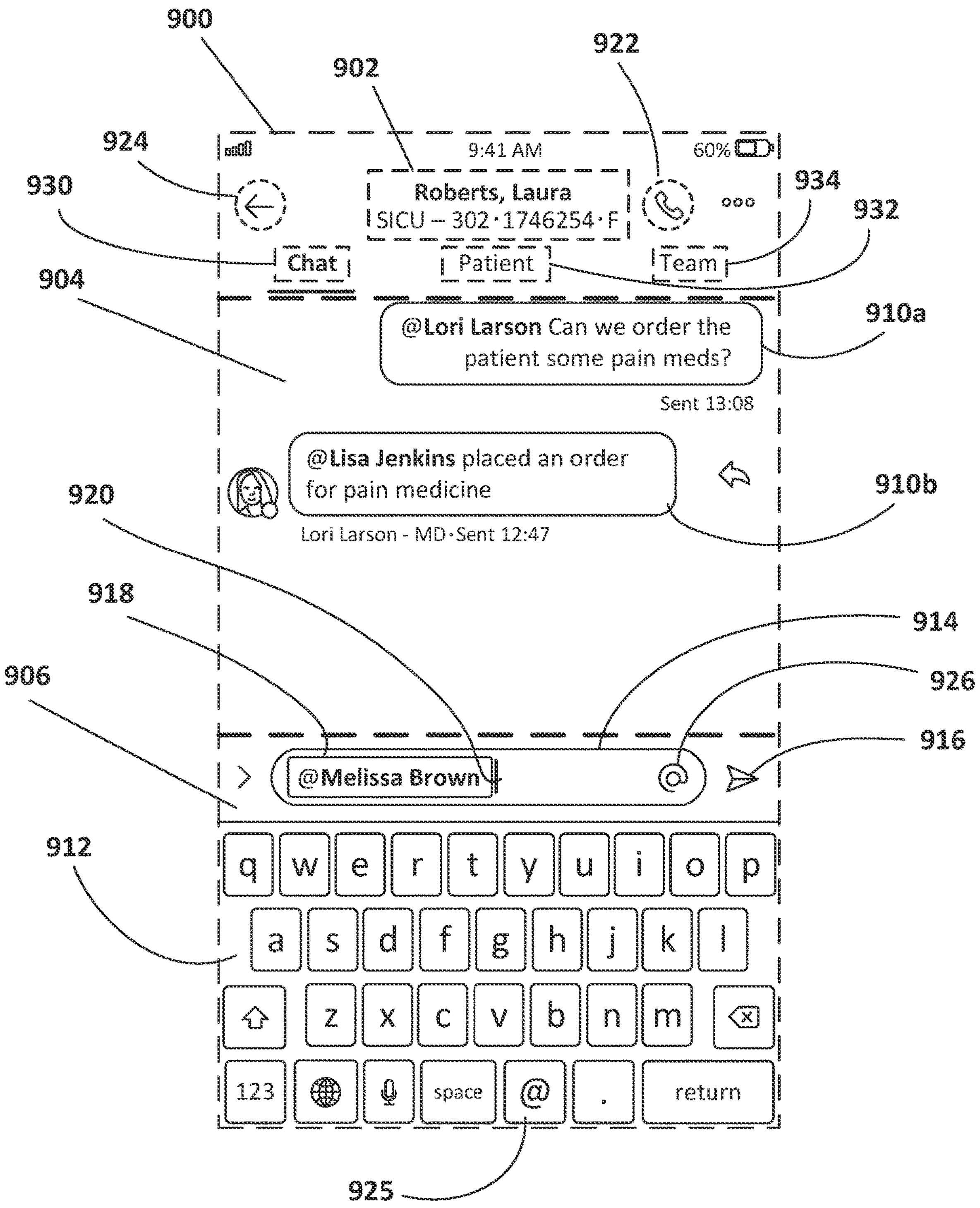
FIG. 9 shows an example of a chat room that can be displayed on a mobile device of a caregiver.

FIG. 9 is an illustrative example of a chat room 900 that can be displayed on a display screen of a mobile device 52 of a caregiver. While FIG. 9 shows a patient-centric chat room, a shift-centric chat room may include many similar features as the chat room 900 such that the following description may apply to patient-centric and shift-centric chat rooms, alike.

Referring now to FIG. 9, the chat room 900 includes a label area 902, a message area 904, and an input area 906. The label area 902 identifies the patient that is the subject of a patient-centric chat room, or the department, unit, or team that is the subject of a shift-centric chat room. In the illustrative example of FIG. 9, the label area 902 identifies a patient as "Roberts, Laura". In patient-centric chat rooms, the label area 902 may provide additional patient details such as the department or unit within the healthcare facility where the patient is admitted (e.g., a Surgical Intensive Care Unit (SICU)), the patient's room number (e.g., "302"), the patient's ID number (e.g., "1746254"), and the patient's sex (e.g., "F" for female, or "M" for male). Additional or fewer details may be included in the label area 902.

The message area 904 displays messages that are sent in the chat room 900 when a chat tab 930 is selected. When a patient tab 932 is selected, additional patient information and details (in addition to those displayed in the label area 902) can be displayed in the message area 904. Additionally, when a team tab 934 is selected, a list of caregivers and staff that are assigned to the chat room 900 can be displayed in another user interface.

In the illustrative example of FIG. 9, a first message **910*a* reads "@ Lori Larson Can we order the patient some pain meds?" and a second message 910*b* reads "@ Lisa Jenkins placed an order for pain medicine". As will be described in more detail, the at symbol @ can be used by a caregiver to tag another caregiver assigned to the chat room 900** in a message that is sent to the chat room. Tagging another caregiver can help to ensure that the message is seen by the intended caregiver by alerting them that the message is directed to them.

In certain examples, only the tagged caregivers receive an alert on their mobile device 52 that notifies them that they have been tagged in a message that has been sent to the chat room, while the other caregivers in the chat room that have not been tagged do not receive the alert. This can reduce alert fatigue which occurs when the caregivers are exposed to a large number of frequent alerts that causes them to consequently become desensitized to the alerts.

In certain examples, the display screen of a mobile device 52 can be a touchscreen such that a caregiver can scroll the message area 904 with their finger to read earlier messages that were sent in the chat room 900. In other examples, a caregiver can scroll the message area 904 with an input device such as a mouse to read earlier messages.

In the illustrative example of FIG. 9, the input area 906 includes a keyboard 912 that a caregiver can use to type a text message inside a text entry field 914, and a send symbol 916 to send the message when completed to the other caregivers assigned to the chat room 900. In this illustrative example, the chat room 900 is displayed on a touchscreen device such that the keyboard 912 and send symbol 916 can be selected with the caregiver's fingers. In addition to typed messages, the caregiver can also insert a photo or image into the message.

The keyboard 912 includes the at symbol @ 925 that is used to tag another caregiver in the text entry field 914. Additionally, the text entry field 914 can include a shortcut 926 can be used to select the at symbol @ to tag another caregiver. Tagging another caregiver in a message will be described in more detail below with reference to FIGS. 14-20. After a caregiver 918 is selected for tagging, the message can be typed following the text cursor 920.

In certain examples, the chat room 900 can include a call symbol 922 that can be selected by a caregiver to call another caregiver assigned to the chat room 900. In certain examples, the chat room 900 can allow the caregiver to directly message another caregiver assigned to the chat room 900 instead of sending a message to the chat room 900. Calling or directly messaging another caregiver can be used when an immediate response is needed.

Additionally, the chat room 900 includes a return symbol 924 that can be selected by a caregiver to exit the chat room 900. In some examples, the return symbol 924 when selected returns the caregiver back to the chat rooms tab 800 when the chat room 900 is accessed from the chat rooms tab 800. Alternatively, when the chat room 900 is accessed from a patient record such as an electronic medical record (EMR) stored on the EMR server 94, the return symbol 924 when selected returns the caregiver back to the patient record.

Figure 10:
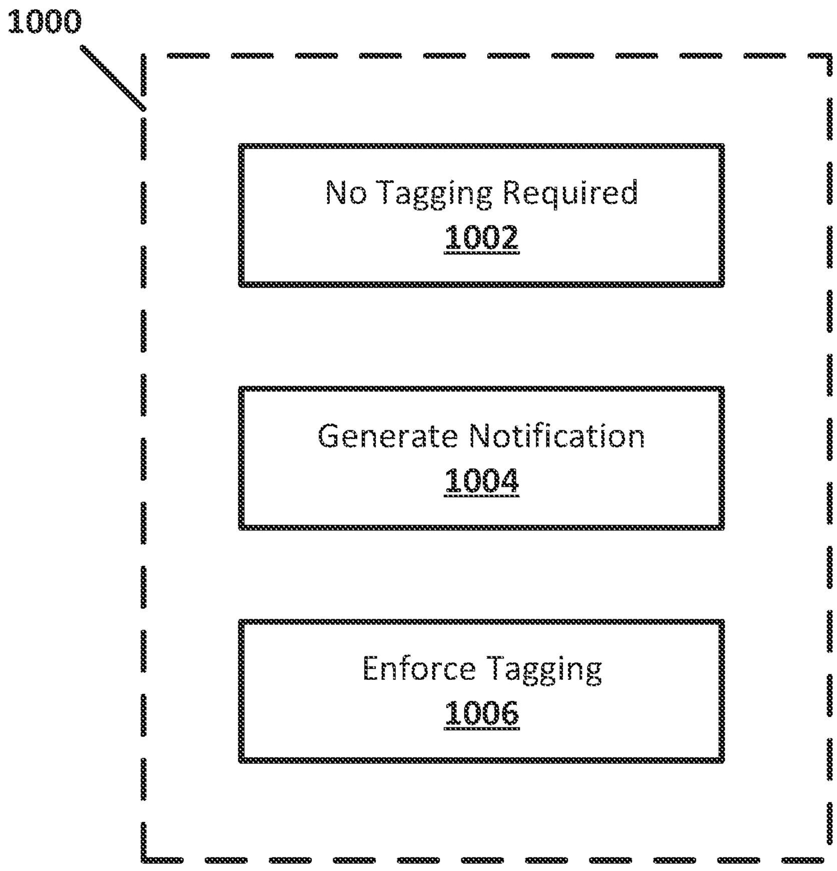
FIG. 10 illustrates levels of tagging protocols for managing messages between caregivers in patient-centric and shift-centric chat rooms.

FIG. 10 illustrates a hierarchy of tagging protocols 1000 for managing messages between caregivers in patient-centric and shift-centric chat rooms. As described above, tagging is identifying or targeting another caregiver in a message to alert them that the message is directed to them. Tagging another caregiver in a message will alert the tagged caregiver that a message pertains to them and is a way to ensure that the message is acknowledged by the intended caregiver. The levels of tagging protocols 1000 include a first level of tagging 1002, a second level of tagging 1004, and a third level of tagging 1006. While three levels of tagging protocols are shown and described herein, the number of tagging protocols may vary as desired.

The mobile caregiver application 200 can allow an administrator to select a tagging protocol for the messaging in the patient-centric and shift-centric chat rooms. In certain examples, the administrator can select one level of tagging protocol for the patient-centric chat rooms, and can select a different level of tagging protocol for the shift-centric chat rooms.

Additionally, the administrator can select a tagging protocol for each patient-centric chat room based on the severity of the patient's condition. For example, the administrator can select a lower-level tagging protocol (e.g., first or second level) for patient-centric chat rooms for patients in good condition, and a higher-level tagging protocol (e.g., third level) for patient-centric chat rooms for patients who have a deteriorated condition.

The first level of tagging 1002 does not require a caregiver to tag another caregiver in order for the caregiver to send a message to the chat room. Thus, a caregiver can simply type and send a message using their mobile device 52, and the message will be sent to the chat room regardless of whether another caregiver has been tagged in the message. The first level of tagging 1002 does not prevent a caregiver from tagging another caregiver in a message.

Figure 11:
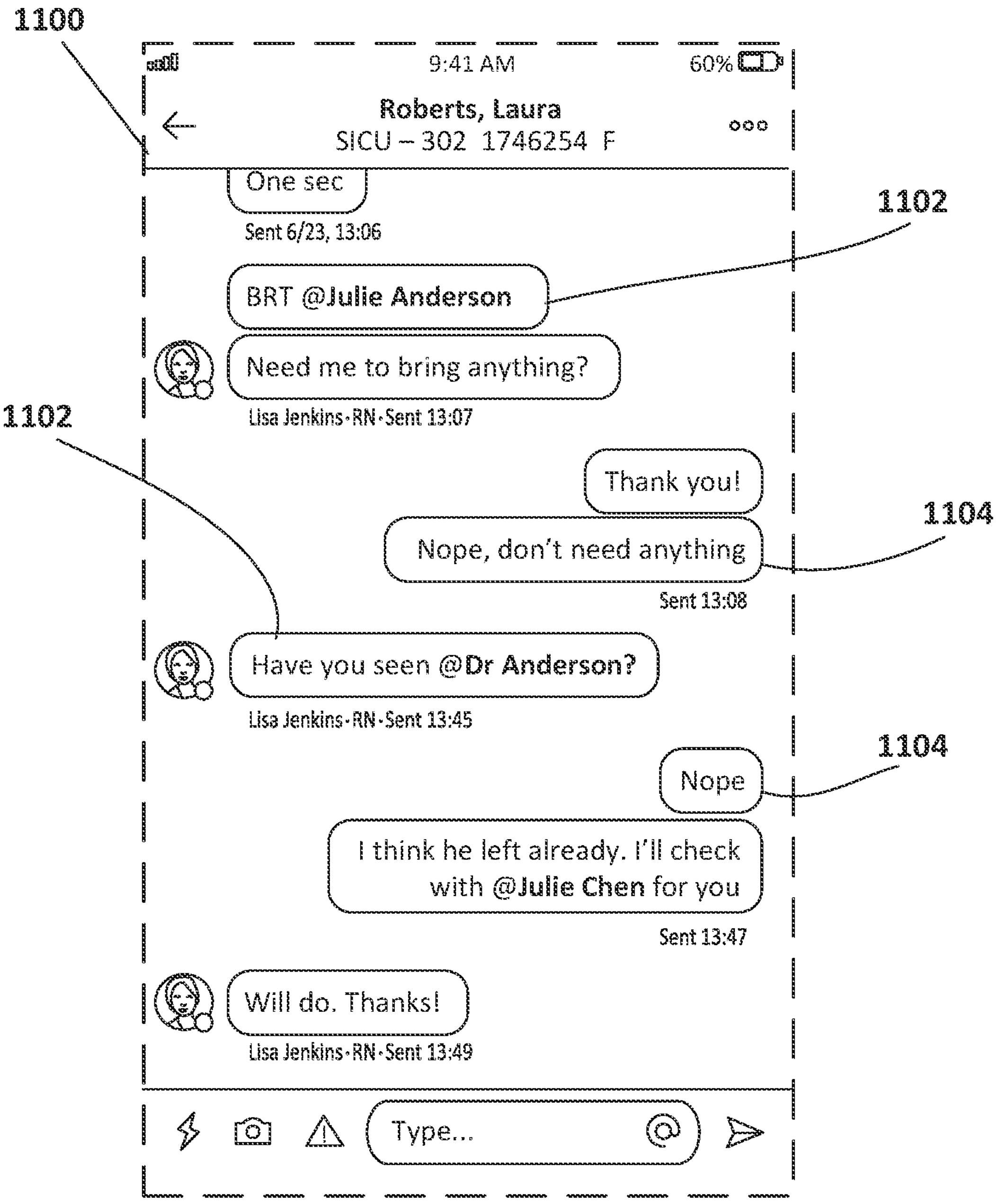
FIG. 11 is another illustrative example of a chat room that can be displayed on a display screen of a mobile device of a caregiver.

FIG. 11 is another illustrative example of a chat room 1100 that can be displayed on a display screen of a mobile device 52 of a caregiver. In the example shown in FIG. 11, the first level of tagging 1002 is supported by the chat room 1100 since at least some messages 1102 tag another caregiver, while other messages 1104 do not tag another caregiver.

The second level of tagging 1004 displays a notification or warning when a caregiver selects the send symbol 916 to send a message to the chat room without tagging another caregiver, however, the notification can be ignored such that the second level of tagging allows the message to be sent to the chat room without tagging another caregiver.

Figure 23:
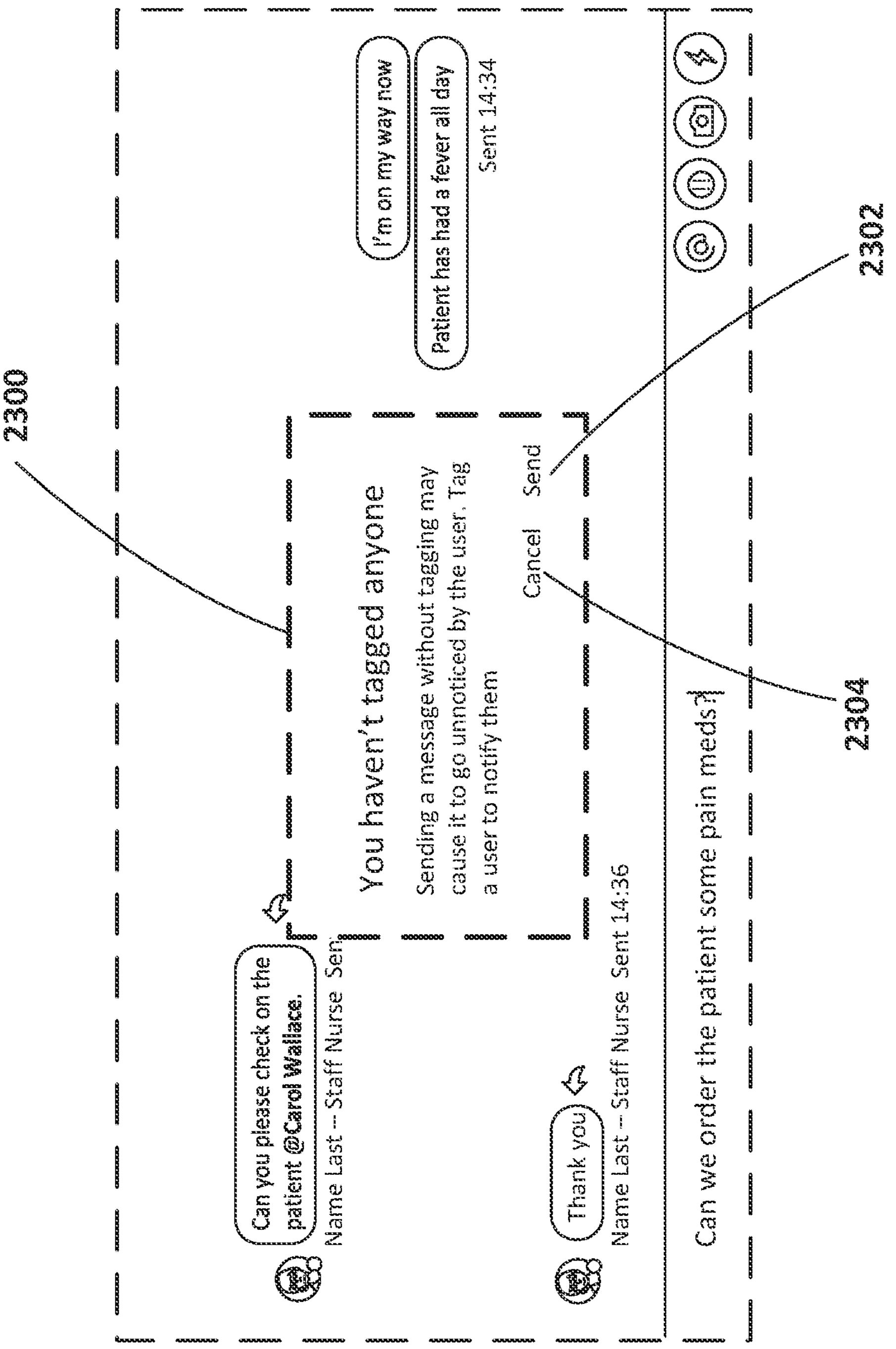
FIG. 23 shows an example of a notification that can be generated when another caregiver is not tagged in message according to the second level of tagging.

FIG. 23 shows an example of a notification 2300 that can be generated when another caregiver is not tagged in message according to the second level of tagging 1004. As shown in FIG. 23, the notification 2300 can include a message that reminds the caregiver to tag another caregiver before the message is sent to the chat room. For example, the notification 2300 can state that "You haven't tagged anyone" and can include further details such as "Sending a message without tagging may cause it to go unnoticed by the user. Tag a user to notify them."

Under the second level of tagging 1004, the notification 2300 provide a send input 2302 which can be selected to send the message without tagging another caregiver. The notification 2300 can also provide a cancel input 2304 that when selected returns the caregiver back to the text entry field so that they can tag another caregiver in the message.

The third level of tagging 1006 enforces tagging by blocking the caregiver from sending a message to the chat room unless another caregiver is tagged. Under the third level of tagging 1006, a notification is generated after the caregiver selects the send symbol 916 to send the message to the chat room without tagging another caregiver. The notification can include a message to remind the caregiver of the need to tag another caregiver such as "Sending a message without tagging may cause it to go unnoticed by the user. Tag a user to notify them."

Unlike the second level of tagging 1004, the caregiver cannot choose to ignore the notification under the third level of tagging 1006. Instead, the caregiver is blocked from sending the message unless they tag another caregiver. Thus, the caregiver must acknowledge the alert, and thereafter revise the message using the keyboard 912 to tag another caregiver.

In addition to making the chat rooms configurable to follow a level of tagging from the hierarchy of tagging protocols 1000, the patient-centric and shift-centric chat rooms can also be equipped with a coaching tool that illustrates how to tag another caregiver in a message. The coaching tool can be automatically displayed when a caregiver enters a chat room for the first time. The coaching tool can provide a short overview of what tagging is and the consequences of not tagging another caregiver when sending a messaging in the chat room. In certain examples, the coaching tool is only displayed the first time the caregiver enters a chat room, and will not be shown on subsequent visits or the first time the caregiver visits other chat rooms. The coaching tool can be helpful for caregivers who are new to the mobile caregiver application 200 and are unfamiliar with how to tag another caregiver in a message for sending to the chat room.

Figure 12:
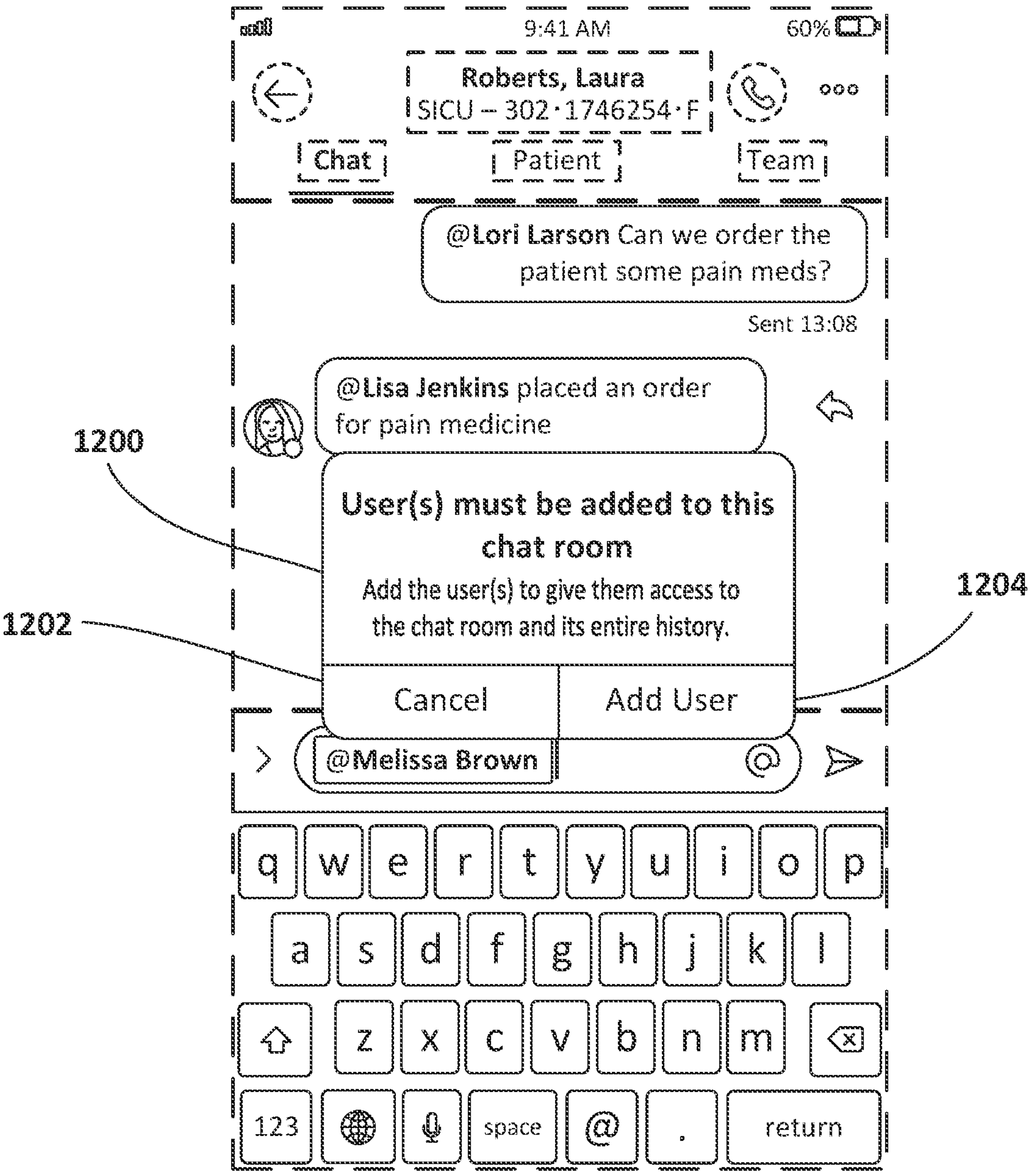
FIG. 12 shows an example of an alert that is displayed when a caregiver attempts to tag another caregiver who is not assigned to the chat room.

FIG. 12 shows an example of an alert 1200 that is displayed when a caregiver attempts to tag another caregiver who is not assigned to the chat room. The alert 1200 can be displayed after the caregiver selects the send symbol 916 to send a message that tags the other caregiver. Alternatively, the alert can be displayed after the other caregiver is recognized by the mobile caregiver application 200, and before the send symbol 916 is selected to send the message. The alert 1200 is displayed over the message area of the chat room.

As shown in FIG. 12, the alert 1200 can include a cancel input 1202 that is selectable to cancel the message and return back to typing the message in the input area 906 of the chat room. Also, the alert 1200 includes an add user input 1204 that can be selected by the caregiver to add the caregiver who is not assigned to the chat room. In some examples, only caregivers who have appropriate credentials are allowed to be added to the chat room. In the example of a patient-centric chat room, only caregivers who have patient viewing privileges (PVP) can be selected to be added to the patient-centric chat room. This can ensure that only qualified caregivers are included in the chat room, and also protect patient privacy.

Figure 13:
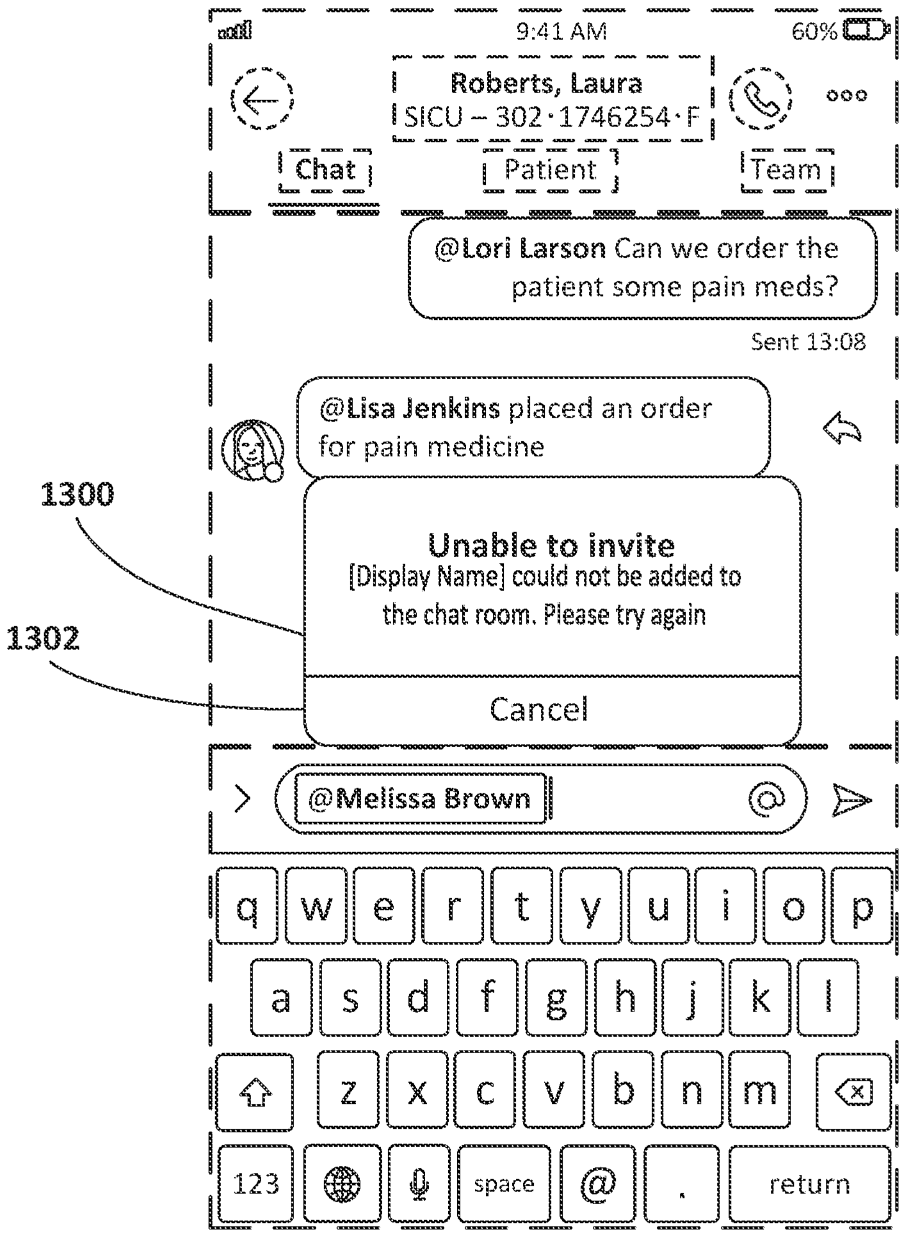
FIG. 13 shows an example of an alert that is generated when a tagged caregiver does not have the appropriate credentials to be added to the chat room.

FIG. 13 shows an example of an alert 1300 that is generated when a tagged caregiver does not have the appropriate credentials to be added to the chat room. As shown in FIG. 13, the alert 1300 can include a message such as "Unable to Invite". The alert 1300 may also include additional details such as "[display name] could not be added to the chat room. Please try again." The alert 1300 includes a cancel input 1302 that is selectable to cancel the message and return back to typing the message in the input area 906 of the chat room.

Figure 14:
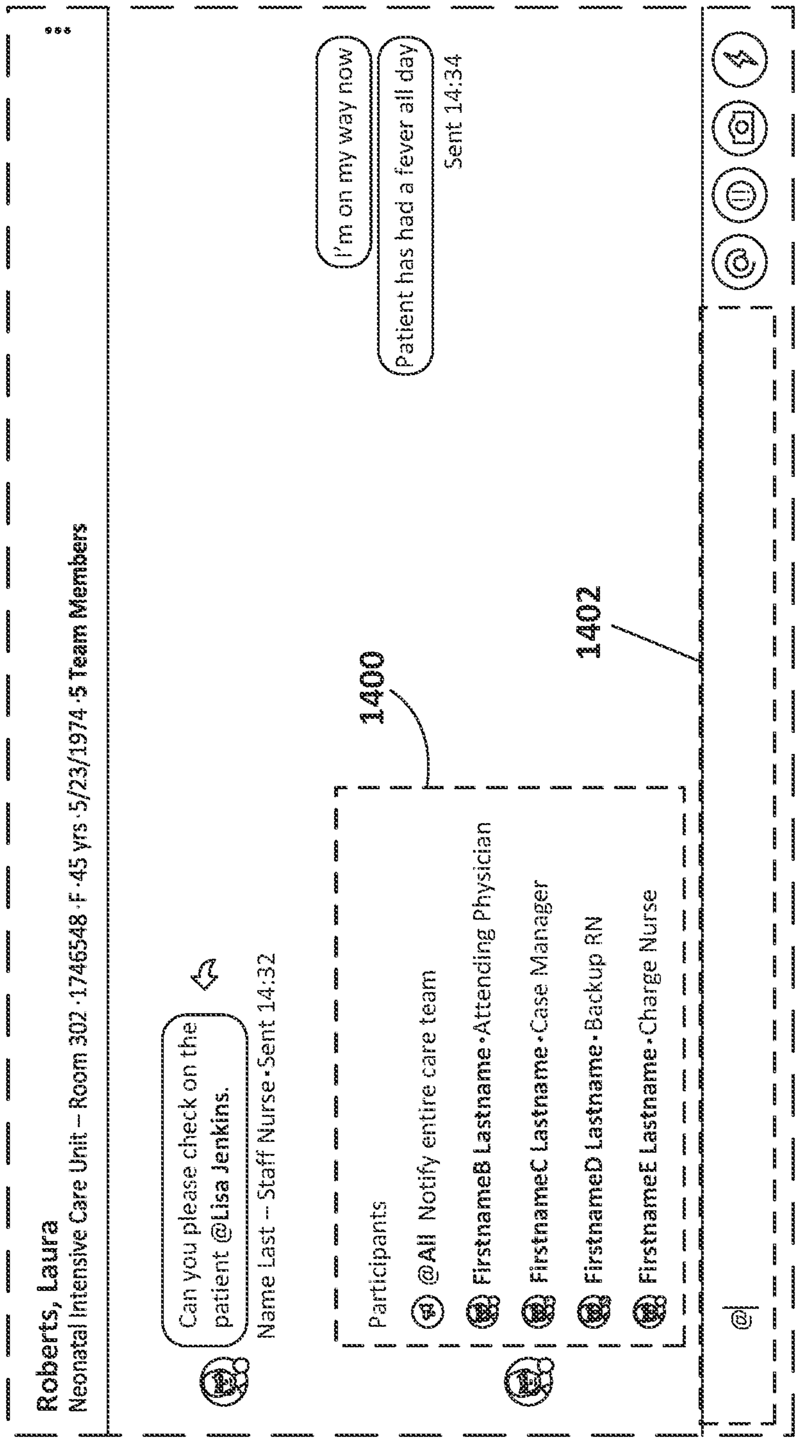
FIG. 14 shows an example of a tag overlay that is displayed when a caregiver attempts to tag another caregiver.

FIG. 14 shows an example of a tag overlay 1400 that is displayed when a caregiver attempts to tag another caregiver inside the text entry field 1402. Once the at symbol @ is entered into the text entry field 1402, the software module 208 displays inside the tag overlay 1400 a list of caregivers that are assigned to the chat room for selection by the caregiver. In certain examples, the list of caregivers is dynamically updated and/or filtered to match the letters that are typed after the at symbol @. Selecting one of the suggested caregivers listed in the tag overlay 1400 will auto-complete the selected caregiver's name in the text entry field 1402, and the caregiver can thereafter continue to type the message inside the text entry field 1402.

In some examples, when a caregiver attempts to add text or an image to a message, the tag overlay 1400 and/or text entry field 1402 are automatically adjusted to ensure that the tag overlay 1400 remains viewable while the caregiver types their message. To ensure that the caregiver is able to view both the text entry field 1402 and the tag overlay 1400 simultaneously, a preview of the image that is added to the message is resized, and/or the text entry field 1402 and the tag overlay 1400 are resized. Additionally, the caregivers listed in the tag overlay 1400 can be truncated for space. For example, the role of each caregiver can be truncated by using an ellipsis (e.g., " . . . "). If space is still needed, the names of the caregivers can also be truncated, and the role of each caregiver is removed entirely. Also, the number of caregivers that are listed in the tag overlay 1400 can be adjusted to create additional spaced.

In the example shown in FIG. 14, only caregivers that are assigned to the chat room and that are on shift are displayed in the tag overlay 1400. The list of caregivers displayed in the tag overlay 1400 is dynamically updated and will immediately display changes when taggable caregivers are added or removed from the chat room.

Also, in addition to tagging another caregiver, an entire team or group of caregivers assigned to the patient can be tagged in a message that is typed in the text entry field 1402. Also, in some examples, a caregiver can tag every member of the chat room by typing @all.

Figure 15:
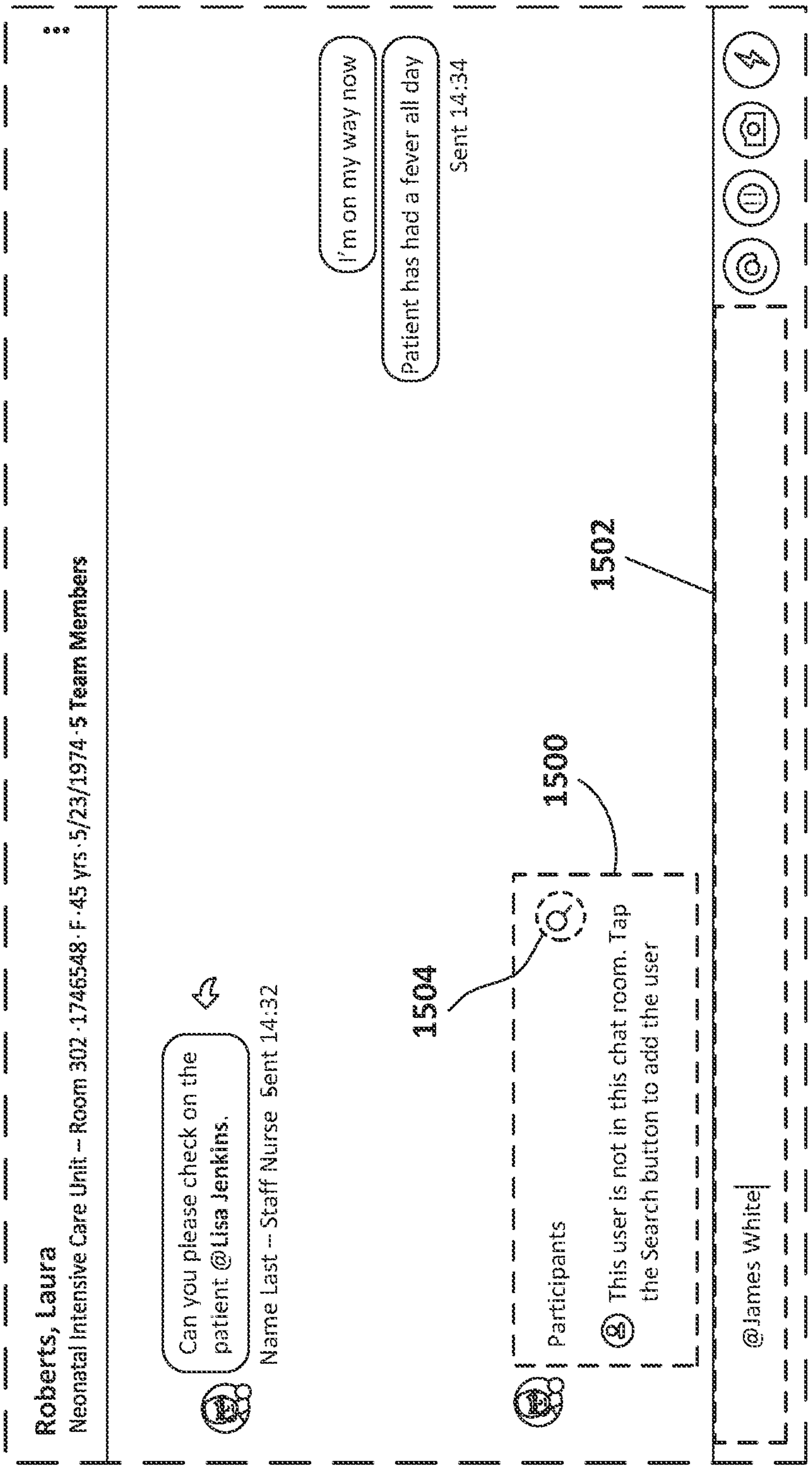
FIG. 15 shows an example of a tag overlay that is displayed when a caregiver attempts to tag another caregiver that is not a member of the chat room.

FIG. 15 shows another example of a tag overlay 1500 that is displayed when a caregiver attempts to tag in a text entry field 1502 another caregiver that is not a member of the chat room. Referring now to FIG. 15, the tag overlay 1500 can include a message such as "This user is not in this chat room." Additionally, the tag overlay 1500 can prompt the caregiver to use the search option 1504 to add the other caregiver to the chat room. For example, the tag overlay 1500 can display a message such as "Tap the search button to add the user."

Figure 16:
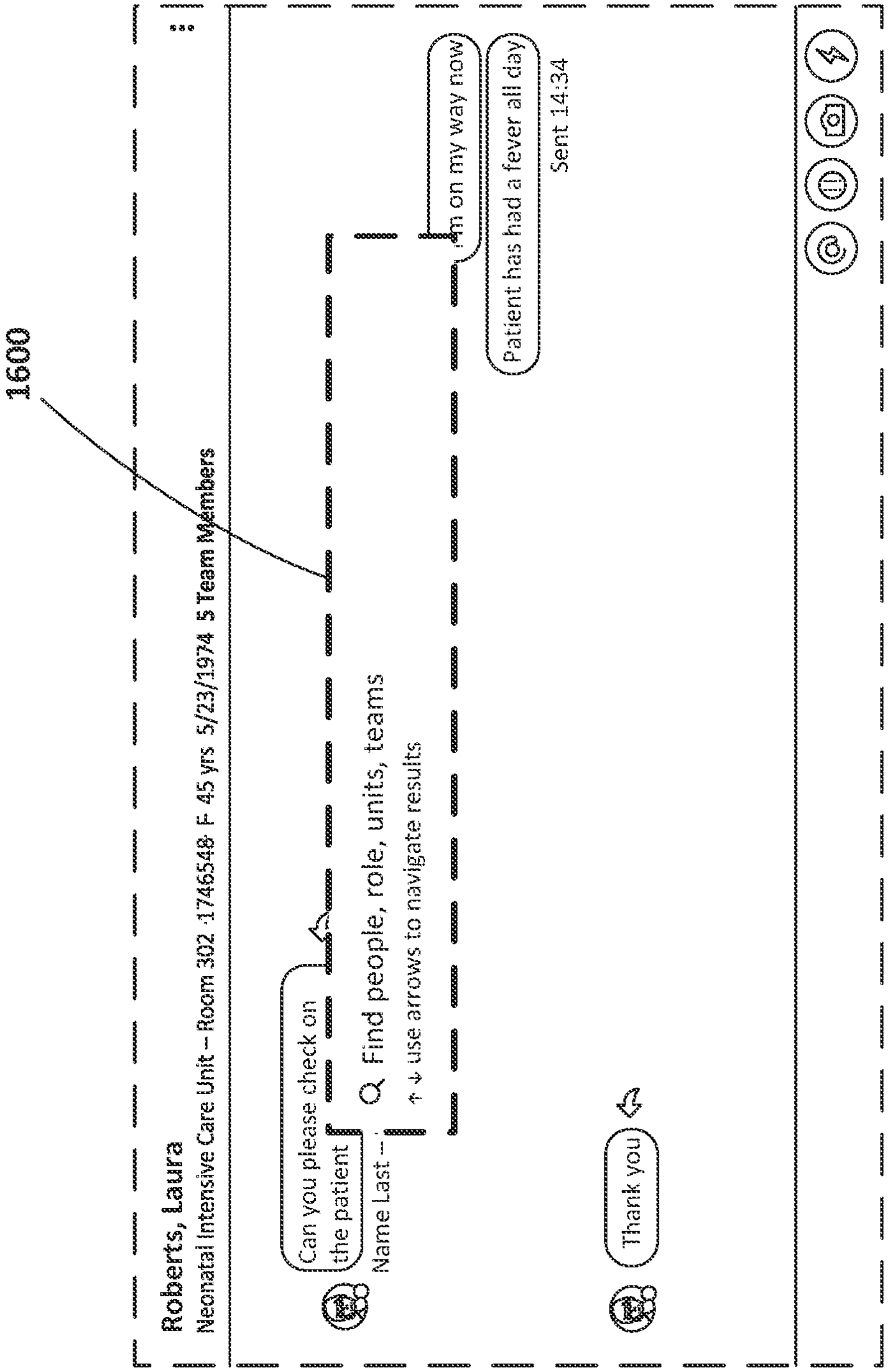
FIG. 16 shows an example of a search overlay that is displayed when a caregiver attempts to add another caregiver that is not a member of the chat room.

FIG. 16 shows an example of a search overlay 1600 that is displayed when a caregiver attempts to add another caregiver that is not assigned to the chat room by selecting the search option 1504 shown in the tag overlay 1500 of FIG. 15. Referring now to FIG. 16, once the search overlay 1600 is opened, the caregiver can search for one or more caregivers to add to the chat room by name, role, unit, or team. Thereafter, the caregiver can select from the search results a caregiver to add to the chat room. As discussed above, only caregivers with credentials such as patient viewing privileges (PVP) can be added to a patient-centric chat room.

Figure 17:
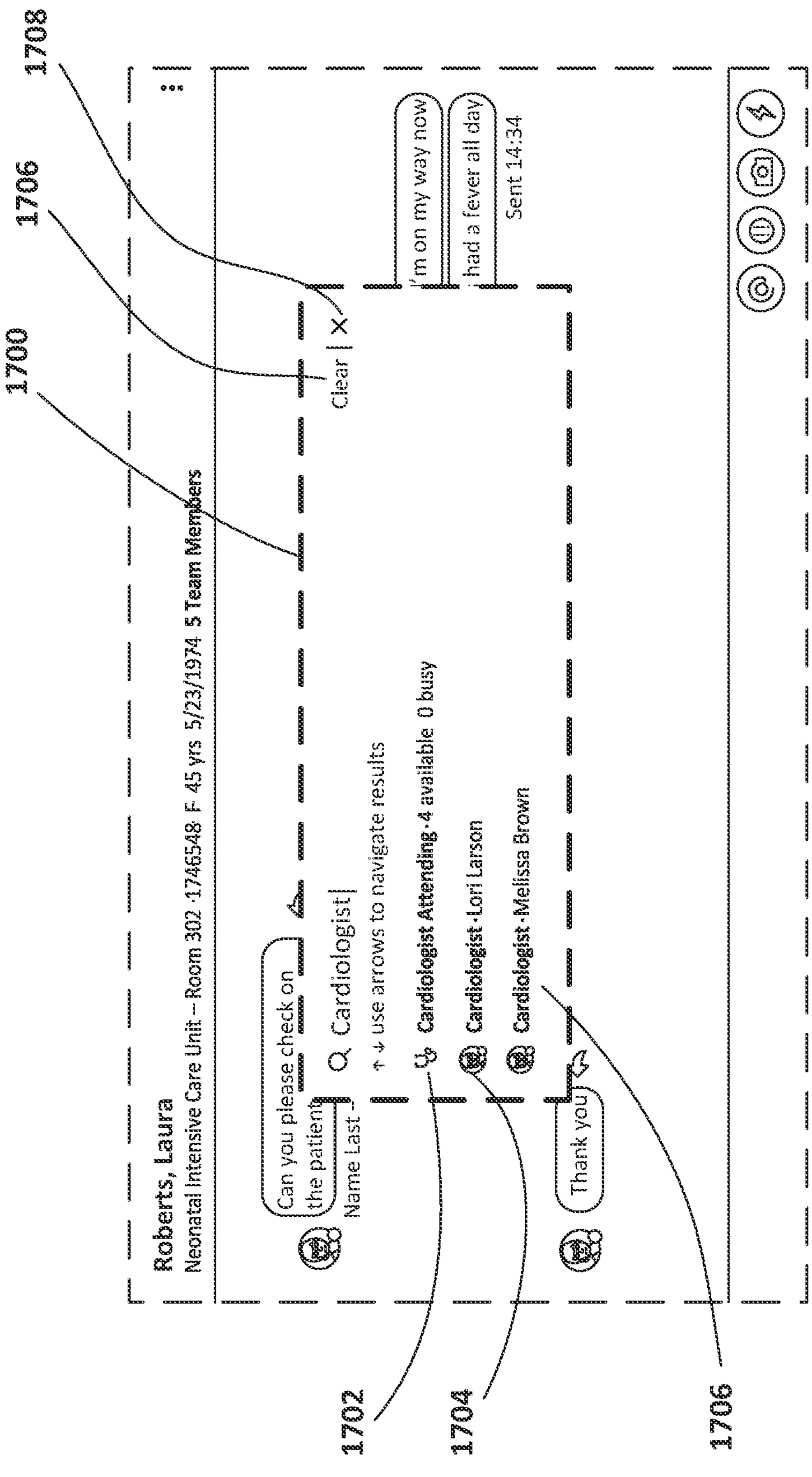
FIG. 17 shows an example of a search overlay that is displayed when a caregiver attempts to add a caregiver or a team of caregivers to the chat room.

FIG. 17 shows an example of a search overlay 1700 that is displayed when a caregiver attempts to add another caregiver to the chat room. In FIG. 17, when the caregiver types "Cardiologist" the search results can include an unnamed cardiologist identified by their status such as Cardiologist Attending 1702, and as well as named cardiologists 1704 such as "Cardiologist—Lori Larson" and "Cardiologist—Melissa Brown". The caregiver can select the Cardiologist Attending 1702 or the named cardiologists 1704 from the search results to add that caregiver to the chat room, or can select clear input 1706 to clear the search and start over, or select exit input 1708 to leave the search overlay 1700 and return to typing their message.

Figure 18:
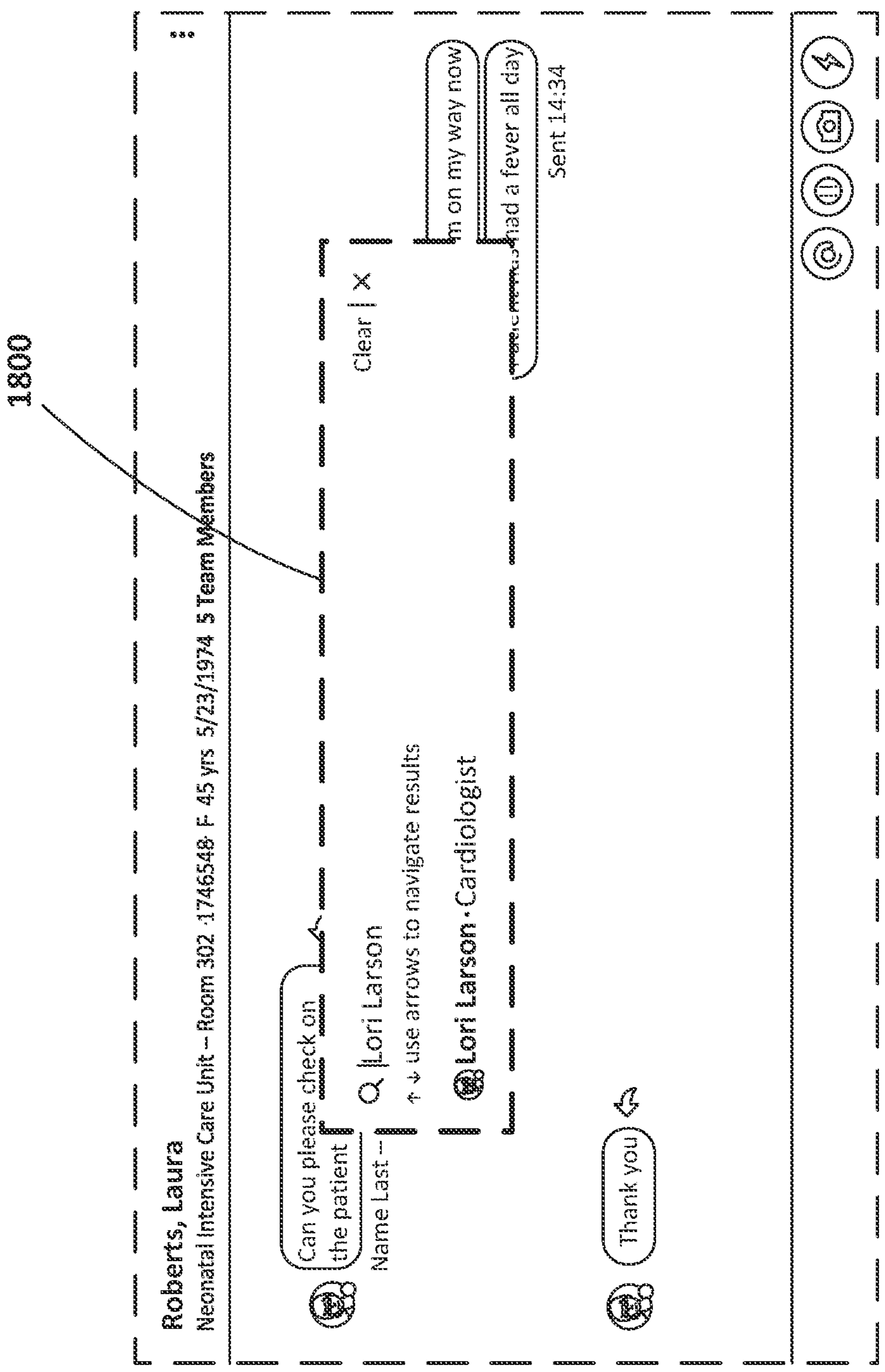
FIG. 18 shows another example of a search overlay that is displayed when a caregiver attempts to add a specific caregiver to the chat room.

FIG. 18 shows another example of a search overlay 1800 that is displayed when a caregiver attempts to search for a specific caregiver to add to the chat room. In the example provided in FIG. 18, in response to the caregiver typing "Lori Larson", the search overlay identifies "Lori Larson—Cardiologist" as matching the search criteria. Thus, the search results provided in the search overlay depend on the specificity of the search criteria. For example, more search results are provided for broad search criteria (e.g., "Cardiologist" of FIG. 17), and fewer search results are provided for specific search criteria (e.g., "Lori Larson" of FIG. 18).

When the desired caregiver is selected from the list displayed in the search overlay 1700, the name of the selected caregiver is displayed as a tag in the message draft. Once the caregiver selects to send the message (i.e., by selecting the send symbol 916) a confirmation can be displayed to confirm that the new caregiver has been added to the chat room. If the tagged caregiver is offline or they no longer have PVP, then an error message (see the alert 1300 of FIG. 13) can be displayed after the caregiver attempts to send the message.

In certain examples, a caregiver can save a draft message before deciding to send the message to the chat room. In examples where the saved draft message tags another caregiver, the tag in the draft message persists when the saved draft message is opened at a later time. In some examples, when a saved draft message contains a tagged caregiver that has been removed from the chat room, the tag in the saved draft message will not persist and the "@username" can be reverted to plain text. In other examples, when a saved draft message tags another caregiver, the tag will persist even if the tagged caregiver is no longer a member of the chat room, and the tagged caregiver will be invited back into the chat room when the draft message is sent.

Figure 21:
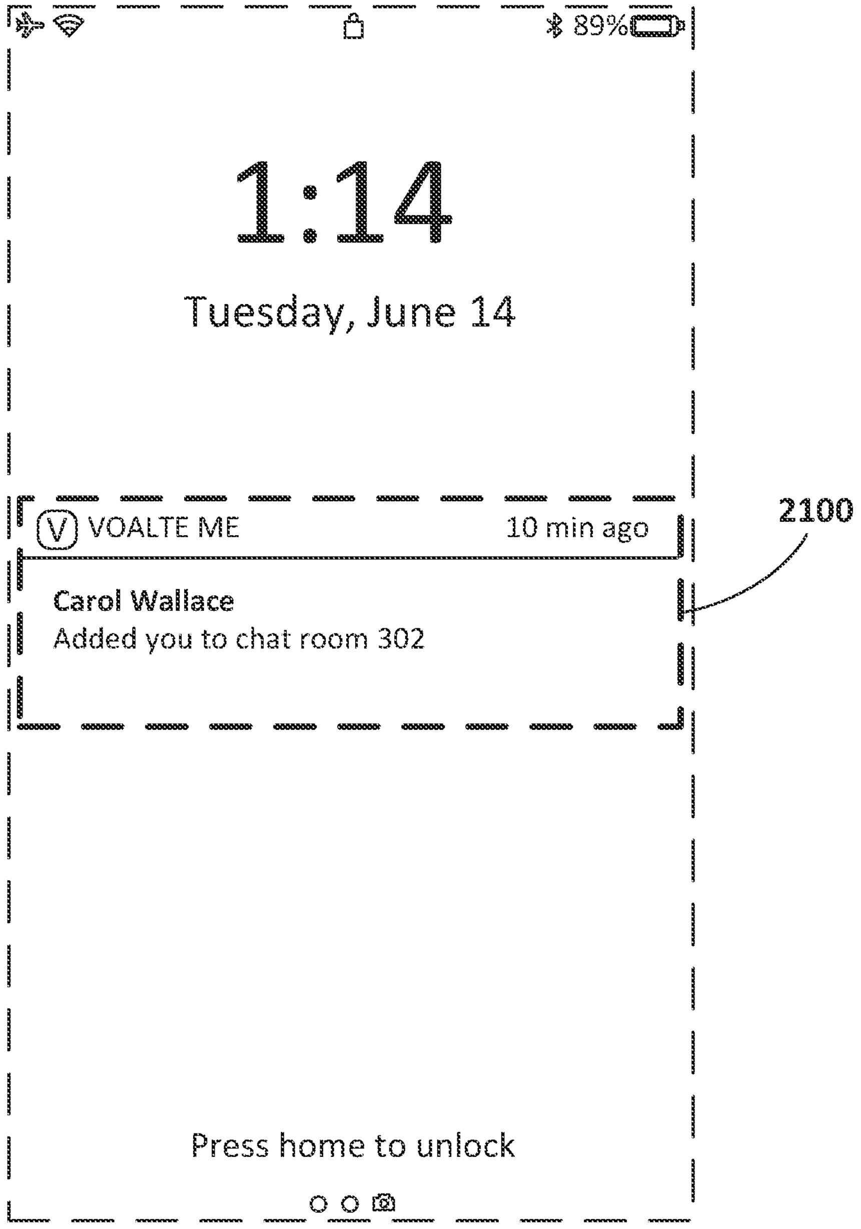
FIG. 21 shows an example of a notification sent to an invited caregiver.

When a tagged caregiver is online and has the appropriate credentials to be added to the chat room, the tagged caregiver will receive a notification that they have been added to the chat room and a join in-line message will be shown in the chat room history to all participants. FIG. 21, shows an example of a notification 2100 that is sent to the invited caregiver. In the example provided in FIG. 21, the notification 2100 can include the name of the chat room such as a patient room (e.g., "chat room 302") in the case of a patient-centric chat room.

Figure 22:
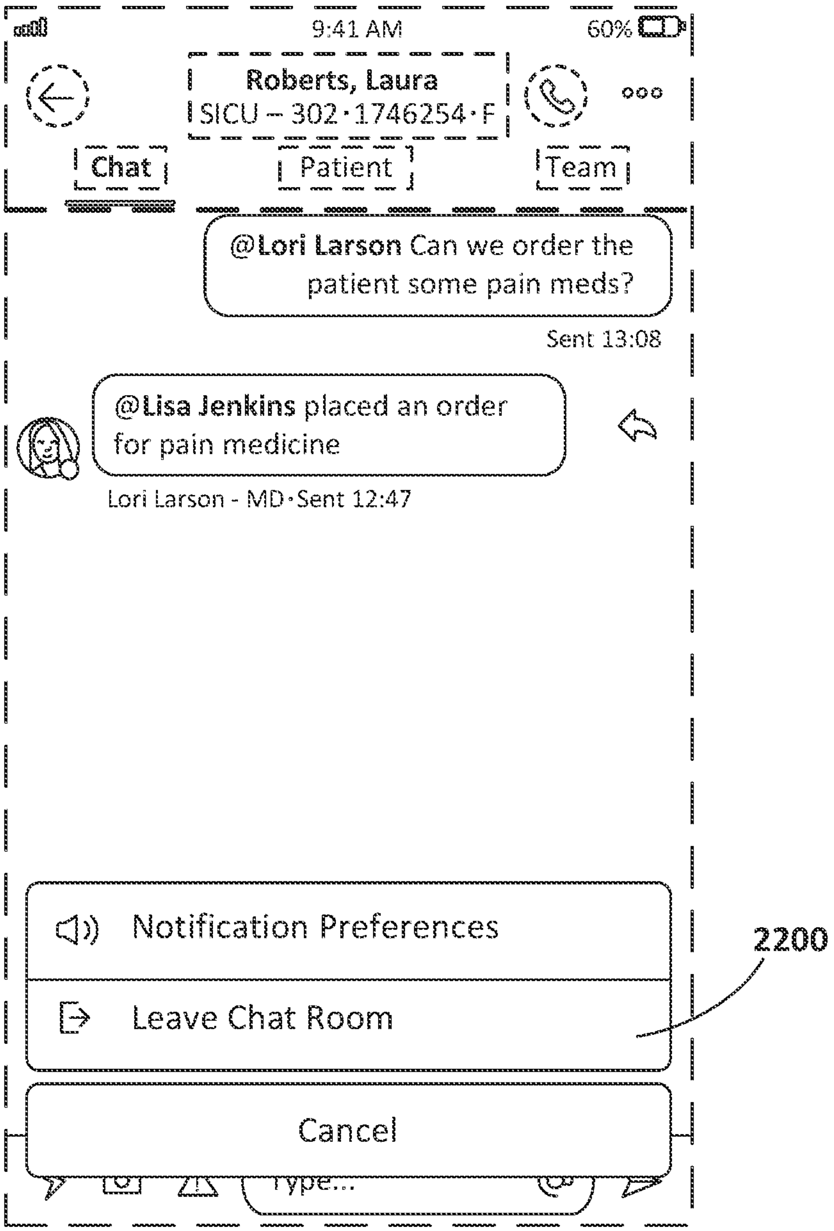
FIG. 22 shows a leave chat room option for an invited caregiver.

When the other caregiver is invited to the chat room, the other caregiver can decide to leave the chat room. In this regard, FIG. 22 shows a leave chat room option 2200 for a caregiver that has been invited to a chat room from another caregiver, but is not assigned to the patient or the patient's room in the case of patient-centric chat rooms, or is not a member of the department, unit, or team in the case of shift-centric chat rooms. Thus, the invited caregiver can leave a chat room without requesting permission to do so from the other caregivers.

Additionally, in some examples, the chat rooms will respect each caregiver's notification preferences. For example, caregivers invited to a chat room can select notification levels for that chat room such as: (1) a mute notification level where no notification or sound for a new message is generated; (2) a tags only notification level where notification and sound are played only for new messages where the invited caregiver is tagged or a group tag (@all) is sent; or (3) an all new messages notification level where notifications are displayed and sounds are played for all new messages received in the chat room except for in-line join/leave messages.

Depending on the notification level for each chatroom, the following events can occur when a new message is received in a chat room: Unread message count on the chat room and chat history tab can iterate. Caregiver can receive an OS notification with or without sound.

When a caregiver leaves a chat room or is removed from the chat room because they are no longer assigned to the patient, or when the chat room is terminated because the patient has been discharged, a banner or message is displayed in the chat room to indicate that the caregiver is no longer a member of the chat room, or that the chat room has been terminated. At this time, the caregiver cannot interact with the chat room anymore and the chat room will be removed from the chat rooms tab 800 displayed on the mobile device 52 of the caregiver. Also, any open notifications/reminders from the chat room are canceled. If a caregiver enters a chat room from a push notification that is generated for a message sent in the chat room, a similar message that indicates that the caregiver is no longer a member of the chat room, or that the patient has been discharged can be displayed and the user is prevented from interacting with the chat room.

Figure 19:
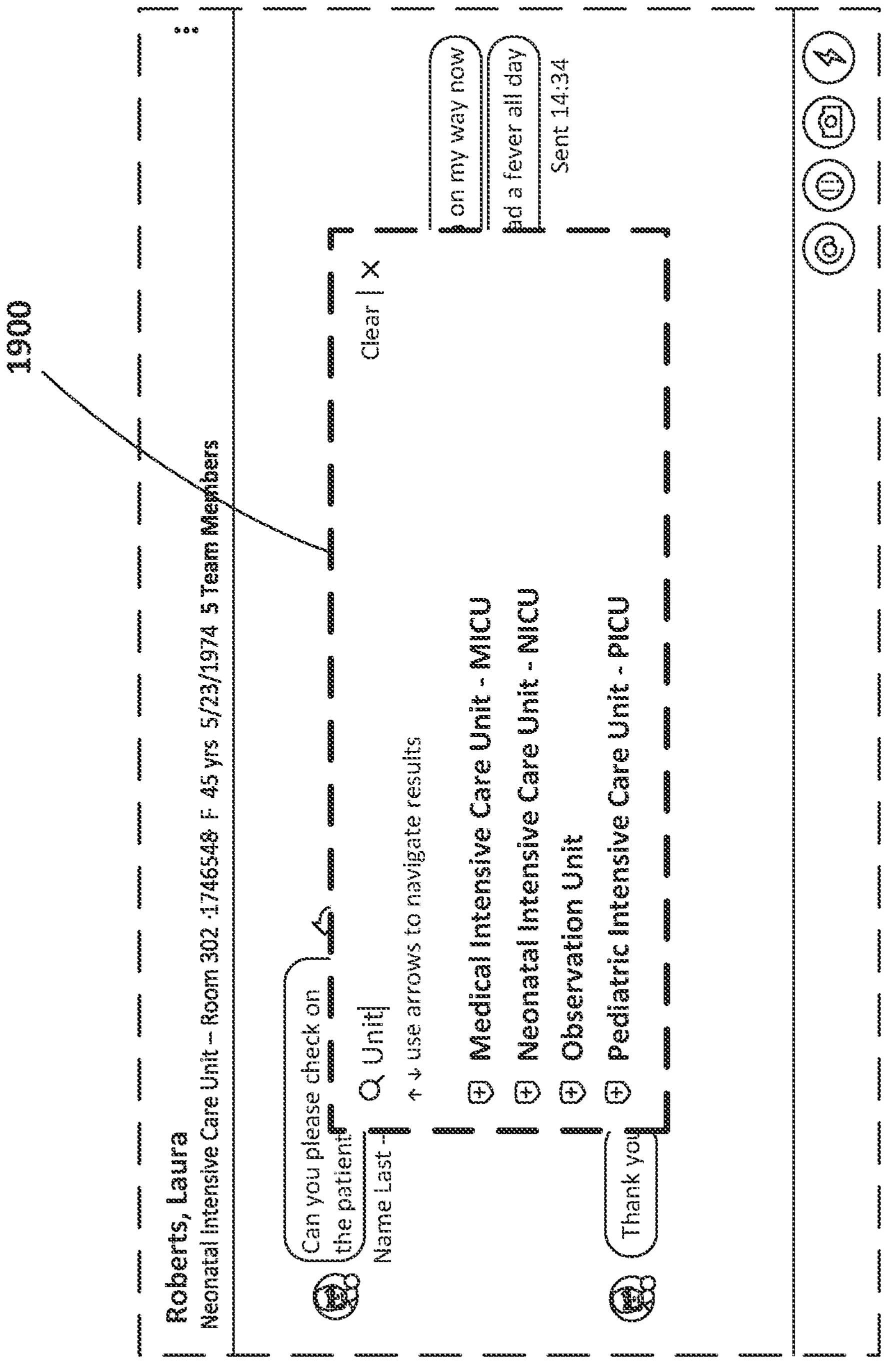
FIG. 19 shows another example of a search overlay that is displayed when a caregiver attempts to add a unit of caregivers to the chat room.

FIG. 19 shows another example of a search overlay 1900 that is displayed when a caregiver attempts to add a unit of caregivers to the chat room. In the example provided in FIG. 19, in response to the caregiver typing "Unit", the search overlay generates a list of healthcare facility units such as a "Medical Intensive Care Unit—MICU", "Neonatal Intensive Care Unit—NICU", "Observation Unit", and "Pediatric Intensive Care Unit—PICU". The units in a healthcare facility may vary from facility to facility such that these search results are provided as illustrative examples that are not meant to be fully enumerated in any way.

Figure 20:
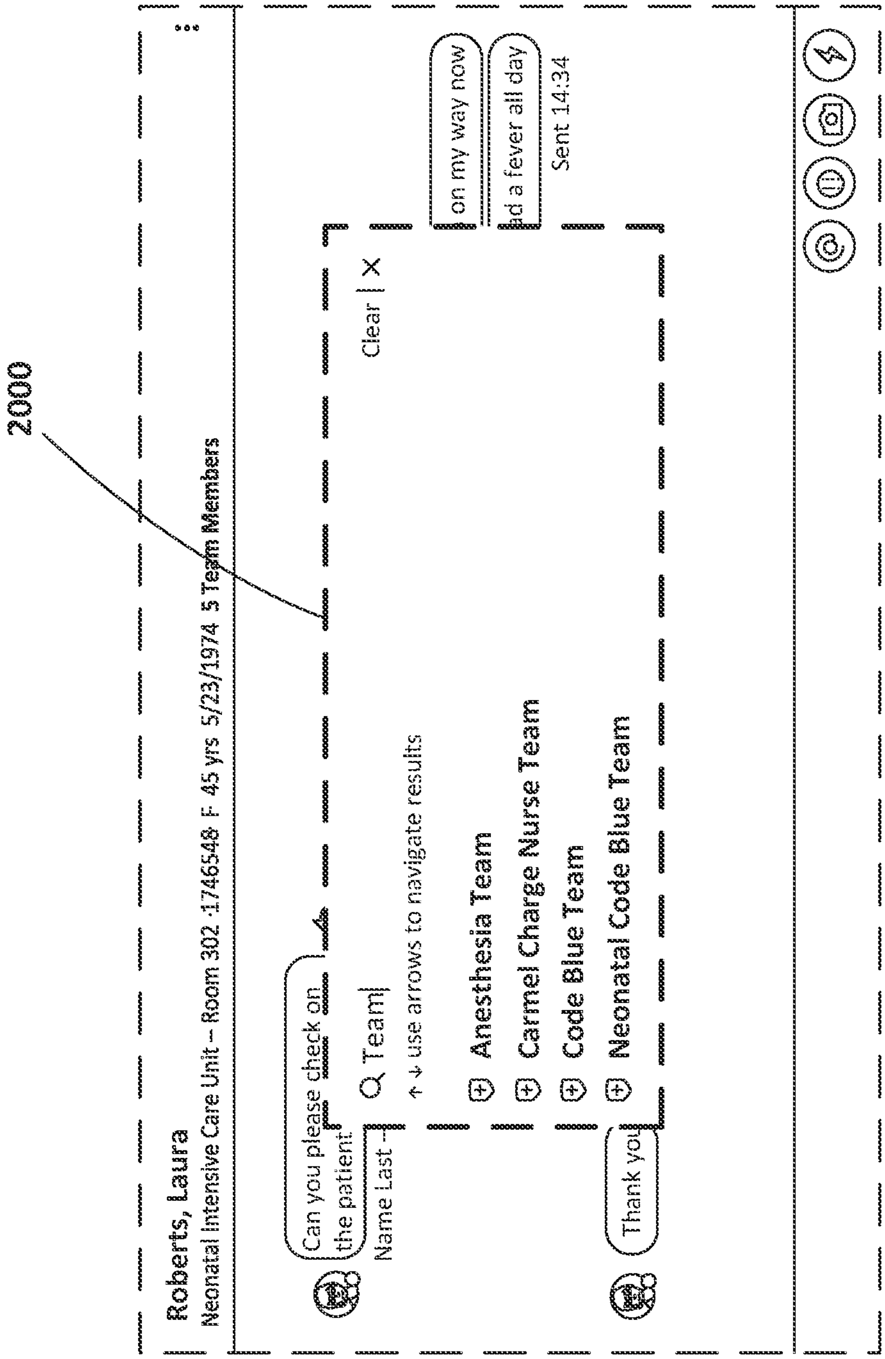
FIG. 20 shows another example of a search overlay that is displayed when a caregiver attempts to add a team of caregivers to the chat room.

FIG. 20 shows another example of a search overlay 2000 that is displayed when a caregiver attempts to add a team of caregivers to the chat room. In the example provided in FIG. 20, in response to the caregiver typing "Team", the search overlay generates a list of healthcare facility teams such as a "Anesthesia Team", "Carmel Charge Nurse Team", "Code Blue Team", and "Neonatal Code Blue Team". The teams of caregivers in a healthcare facility may vary from facility to facility such that these search results are provided as illustrative examples only.

Figure 24:
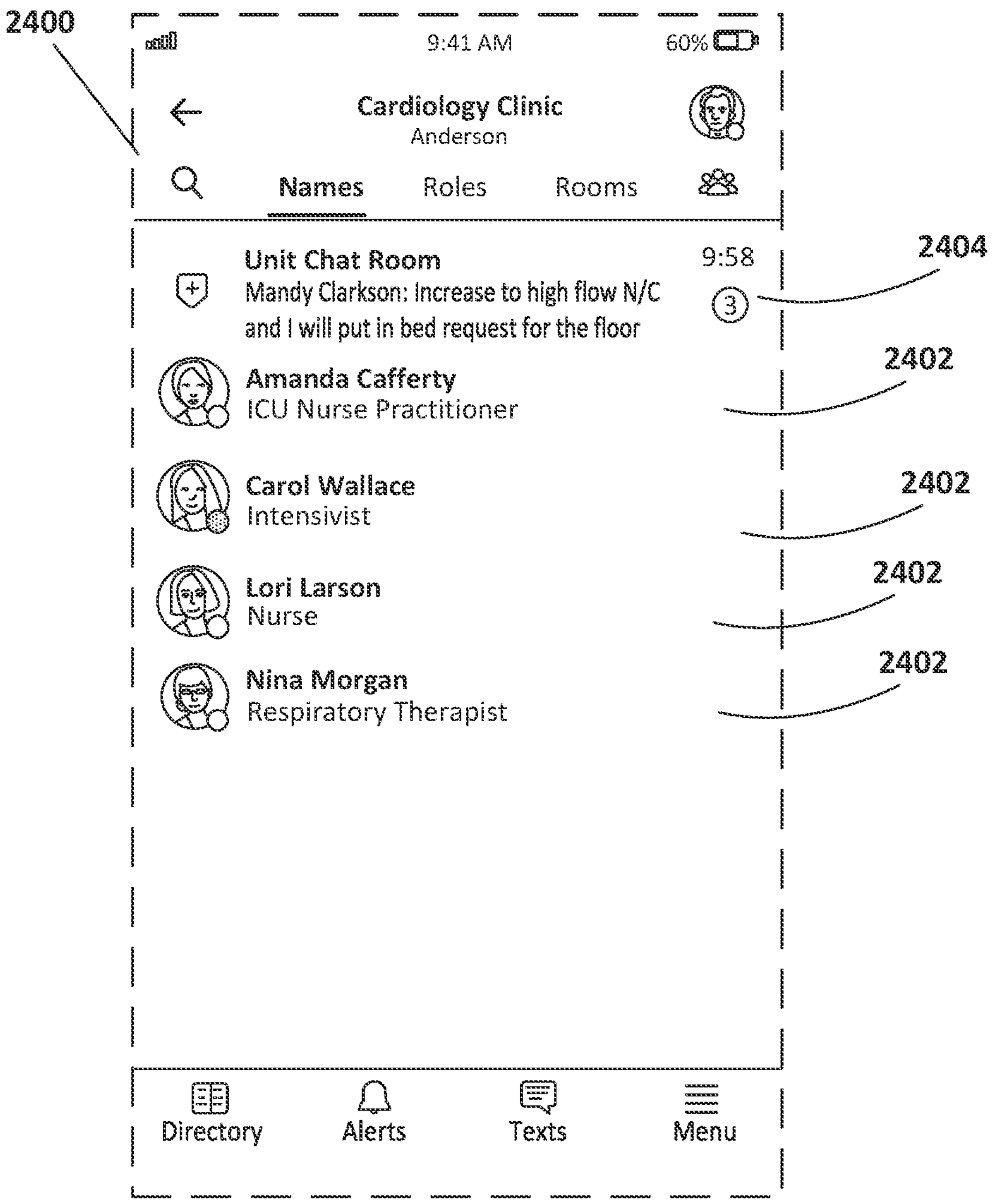
FIG. 24 shows an example of a user interface that can be displayed on a display screen of the mobile device of a caregiver.

FIG. 24 shows an example of a user interface 2400 that can be displayed on a display screen of a mobile device 52 of a caregiver. The user interface 2400 is a shift-centric chat room for a clinic within the healthcare facility (e.g., "Cardiology Clinic"). The user interface 2400 can be displayed in response to a selection of a chat room from the chat rooms tab 800. As shown in FIG. 2400, the user interface 2400 displays a list of the caregivers 2402 that are assigned to the chat room. The user interface 2400 can further display a unit chat room 2404. In certain examples, a caregiver can select a particular caregiver 2402 to message them directly instead of sending a message to the unit chat room 2404. Alternatively, a caregiver can select the unit chat room 2404 to message the entire unit. The role of each caregiver 2402 can be provided such as "ICU Nurse Practitioner", "Intensivist", "Nurse", "Respiratory Therapist", and the like.

Figure 25:
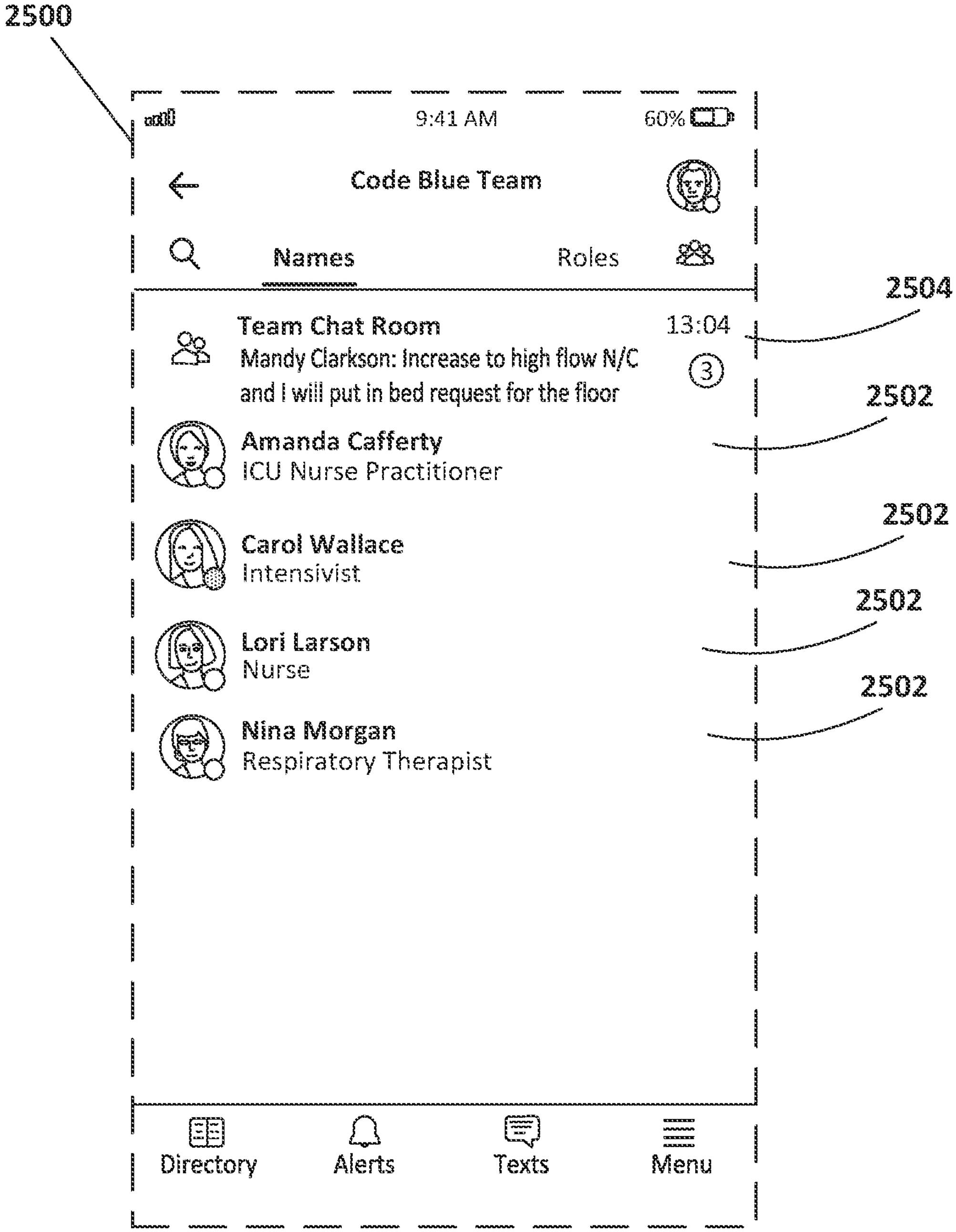
FIG. 25 shows another example of a user interface that can be displayed on a display screen of the mobile device of a caregiver.

FIG. 25 shows another example of a user interface 2500 that can be displayed on a display screen of a mobile device 52 of a caregiver. The user interface 2500 is a shift-centric chat room for a team within the healthcare facility (e.g., "Code Blue Team"). For example, the user interface 2500 can be displayed in response to a selection of the chat room **802*b* shown in FIG. 8. Alternatively, the user interface 2500 can be displayed in response to a caregiver selecting the team tab 934 shown in the chat room 900 of FIG. 9. As shown in FIG. 25, the user interface 2500 displays a list of the caregivers 2502 that are assigned to the chat room. The user interface 2500 can further display a team chat room 2504. In certain examples, a caregiver can select a particular caregiver 2502 to message them directly instead of sending a message to the chat room. Alternatively, a caregiver can select the team chat room 2504** to message the entire team.

Figure 26:
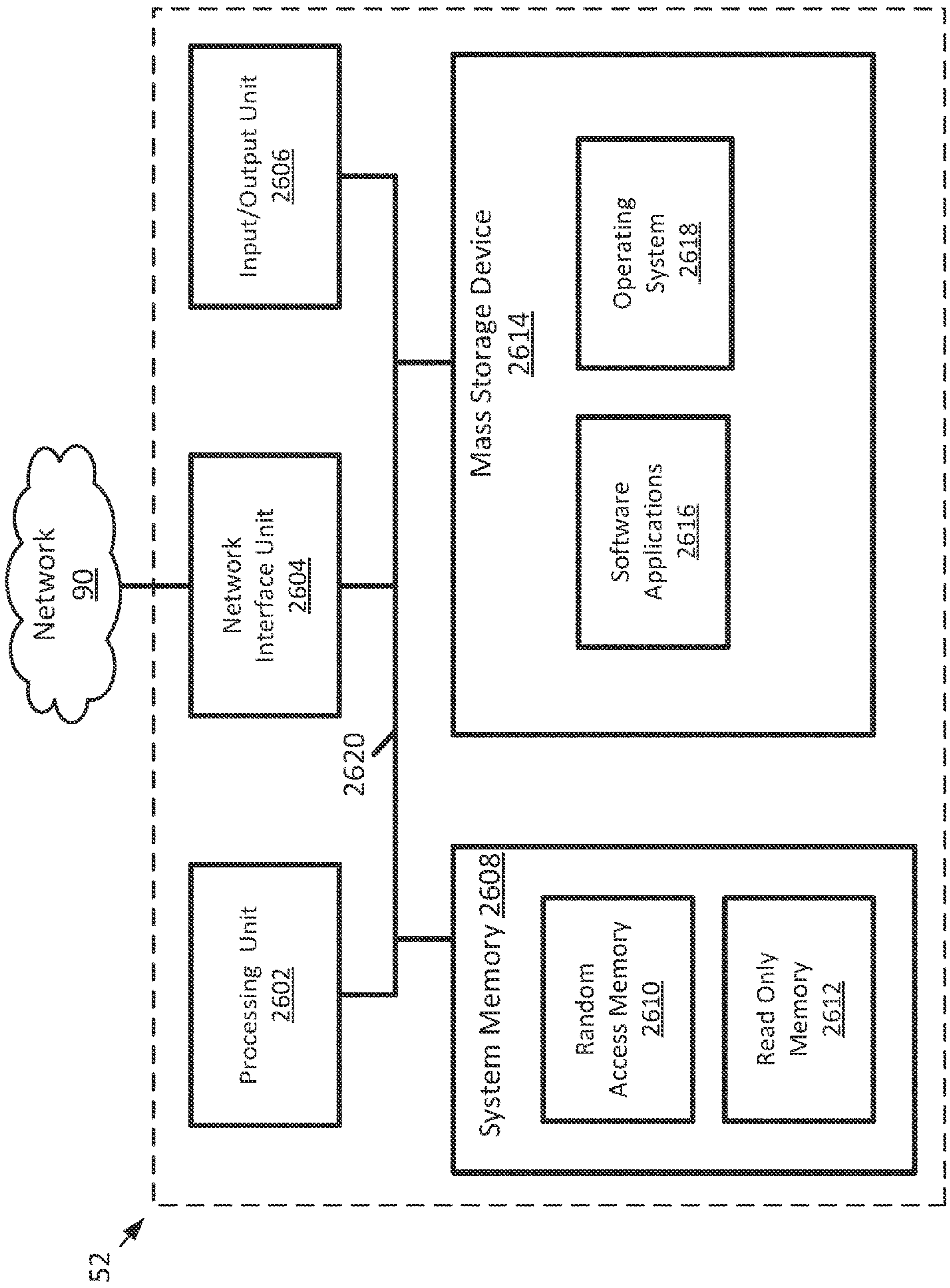
FIG. 26 schematically illustrates an example of one of the mobile devices of the caregiver communications system of FIG. 1.

FIG. 26 schematically illustrates one of the mobile devices 52 which can be used to implement aspects of the present disclosure, such as the functions of the mobile devices 52 equipped with the mobile caregiver application 200. The mobile device 52 includes a processing unit 2602, a system memory 2608, and a system bus 2620 that couples the system memory 2608 to the processing unit 2602. The processing unit 2602 is an example of a processing device such as a central processing unit (CPU). The system memory 2608 includes a random-access memory ("RAM") 2610 and a read-only memory ("ROM") 2612. A basic input/output logic containing the basic routines that help to transfer information between elements within the mobile device 52, such as during startup, is stored in the ROM 2612. Although one of the mobile devices 52 is depicted in FIG. 26, the other computing devices disclosed herein can have similar components.

The mobile device 52 can also include a mass storage device 2614 that is able to store software instructions and data. The mass storage device 2614 is connected to the processing unit 2602 through a mass storage controller (not shown) connected to the system bus 2620. The mass storage device 2614 and its associated computer-readable data storage media provide non-volatile, non-transitory storage for the mobile device 52.

Although the description of computer-readable data storage media contained herein refers to a mass storage device, it should be appreciated by those skilled in the art that computer-readable data storage media can be any available non-transitory, physical device or article of manufacture from which the device can read data and/or instructions. In certain embodiments, the computer-readable storage media comprises entirely non-transitory media. The mass storage device 2614 is an example of a computer-readable storage device.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid-state memory technology, or any other medium which can be used to store information, and which can be accessed by the device.

The mobile device 52 may operate in a networked environment using logical connections to remote network devices, including the server 114, through the network 110, such as a local network, the Internet, or another type of network. The mobile device 52 connects to the network 110 through a network interface unit 2604 connected to the system bus 2620. The network interface unit 2604 may also be utilized to connect to other types of networks and remote computing systems.

The mobile device 52 can also include an input/output controller 2606 for receiving and processing input from a number of input devices. Similarly, the input/output controller 2606 may provide output to a number of output devices.

The mass storage device 2614 and the RAM 2610 can store software instructions and data. The software instructions can include an operating system 2618 suitable for controlling the operation of the device. The mass storage device 2614 and/or the RAM 2610 also store software instructions 2616, that when executed by the processing unit 2602, cause the device to provide the functionality of the device discussed in this document.

The various embodiments described above are provided by way of illustration only and should not be construed to be limiting in any way. Various modifications can be made to the embodiments described above without departing from the true spirit and scope of the disclosure.

What is claimed is:

1. A system for providing communications on mobile devices located in a healthcare facility, the system comprising:

a computing device having a network interface unit, at least one processor, and a memory storing instructions which, when executed by the at least one processor, cause the system to:

couple the network interface unit to:

an admission, discharge, transfer (ADT) server; and an electronic medical records (EMR) server;

receive, from the ADT server via the network interface unit, a first notification identifying a patient admitted to the healthcare facility;

create a patient-centric chat room based on the first notification;

add the caregivers to the patient-centric chat room, each of the caregivers added to the patient-centric chat room having a role that provides patient viewing privileges and being assigned to the patient or to the patient's location in the healthcare facility;

provide messaging communications in the patient-centric chat room for the caregivers to communicate with each other;

determine, based upon patient transfer notifications from the ADT received via the network interface unit, when the patient moves to a new location in the healthcare facility;

automatically update patient-centric chat room membership based upon the patient transfer notifications from the ADT server, including to:

automatically remove from the patient-centric chat room the caregivers that are not assigned to the patient's new location; and automatically add to the patient-centric chat room the caregivers assigned to the patient's new location;

receive, from the ADT server via the network interface unit, a second notification identifying a discharge of the patient from the healthcare facility;

terminate the patient-centric chat room upon the patient being discharged from the healthcare facility, the patient-centric chat room being terminated in response to the second notification identifying the discharge of the patient from the healthcare facility;

communicate, by the network interface unit, messages from the patient-centric chat room to the EMR server for storage thereby reducing storage requirements on the mobile devices of the caregivers; and parse the messages stored in the EMR server for information not otherwise recorded in the EMR server.

2. The system of claim 1, wherein the memory stores further instructions which, when executed by the at least one processor, cause the system to:

configure the messaging communications for a caregiver to tag another caregiver in a message sent to the patient-centric chat room, the tag identifying the another caregiver in the message to alert the another caregiver that the message is directed to them.

3. The system of claim 1, wherein the memory stores further instructions which, when executed by the at least one processor, cause the system to:

provide searching for one or more additional caregivers to add to the patient-centric chat room by searching a name, role, unit, or team of the one or more additional caregivers.

4. The system of claim 1, wherein the memory stores further instructions which, when executed by the at least one processor, cause the system to:

automatically add to the patient-centric chat room new caregivers assigned to the patient based on a change of unit of the patient in the healthcare facility.

5. The system of claim 1, wherein the memory stores further instructions which, when executed by the at least one processor, cause the system to:

automatically remove from the patient-centric chat room the caregivers no longer assigned to the patient based on a change of unit of the patient in the healthcare facility.

6. The system of claim 1, wherein the memory stores further instructions which, when executed by the at least one processor, cause the system to:

remove the caregivers from the patient-centric chat room that have ended their shift; and add the caregivers to the patient-centric chat room that have started their shift, and that have patient viewing privileges, and are assigned to the patient or to the patient's location in the healthcare facility.

7. The system of claim 1, wherein the memory stores further instructions which, when executed by the at least one processor, cause the system to:

generate a warning notification that provides a warning when another caregiver is not tagged in a message to the patient-centric chat room.

8. The system of claim 1, wherein the memory stores further instructions which, when executed by the at least one processor, cause the system to:

block a message from being sent to the patient-centric chat room when another caregiver is not tagged in the message to the patient-centric chat room.

9. A method for providing communications in a healthcare facility, the method comprising:

providing a computing device having a network interface unit, at least one processor, and a memory;

coupling the network interface unit to:

an admission, discharge, transfer (ADT) server; and an electronic medical records (EMR) server;

receiving, from the ADT server via the network interface unit, a first notification identifying a patient admitted to the healthcare facility;

creating a patient-centric chat room based on the first notification;

adding caregivers to the patient-centric chat room, each of the caregivers having a role providing patient viewing privileges, and being assigned to the patient or to the patient's location;

providing messaging communications in the patient-centric chat room for the caregivers to communicate with each other in the patient-centric chat room;

determining, based upon patient transfer notifications from the ADT received via the network interface unit, when the patient moves to a new location in the healthcare facility;

automatically removing from the patient-centric chat room the caregivers that are not assigned to the new location of the patient in the healthcare facility, the new location of the patient being determined based on a message received from the ADT server;

automatically adding to the patient-centric chat room the caregivers assigned to the new location of the patient in the healthcare facility;

receiving, from the ADT server via the network interface unit, a second notification identifying a discharge of the patient from the healthcare facility;

terminating the patient-centric chat room in response to the second notification identifying a discharge of the patient from the healthcare facility;

communicating, by the network interface unit, messages from the patient-centric chat room to the EMR server for storage thereby reducing storage requirements on mobile devices of the caregivers; and parsing the messages stored in the EMR server for information not otherwise recorded in the EMR server.

10. The method of claim 9, further comprising:

automatically removing the caregivers from the patient-centric chat room who have ended their shift in the healthcare facility; and automatically adding new caregivers to the patient-centric chat room who have started their shift in the healthcare facility, the new caregivers having patient viewing privileges and being assigned to the patient or to the patient's location in the healthcare facility.

* * * * *